(12) United States Patent
Anderson et al.

(10) Patent No.: US 9,532,849 B2
(45) Date of Patent: Jan. 3, 2017

(54) SURGICAL ACCESSORY CLAMP AND SYSTEM

(75) Inventors: S. Christopher Anderson, Northampton, MA (US); Thomas G. Cooper, Menlo Park, CA (US); Bruce Schena, Menlo Park, CA (US); William Burbank, Sandy Hook, CT (US); Margaret M. Nixon, Santa Clara, CA (US); Alan Loh, Los Altos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 218 days.

(21) Appl. No.: 13/454,890

(22) Filed: Apr. 24, 2012

(65) Prior Publication Data

US 2012/0209291 A1 Aug. 16, 2012

Related U.S. Application Data

(60) Division of application No. 11/240,087, filed on Sep. 30, 2005, now Pat. No. 8,182,469, which is a
(Continued)

(51) Int. Cl.
*A61B 19/00* (2006.01)
*F16B 2/18* (2006.01)
(Continued)

(52) U.S. Cl.
CPC ............... *A61B 90/57* (2016.02); *A61B 34/37* (2016.02); *A61B 34/71* (2016.02); *A61B 90/50* (2016.02);
(Continued)

(58) Field of Classification Search
CPC ... A61B 19/081; A61B 19/22; A61B 19/2203; A61B 1/00147; A61B 1/00149; A61B 2019/2234; A61B 90/50; A61B 90/57; A61B 2034/305; F16B 2/10; F16B 2/185; F16L 3/1014; F16L 3/1033; Y10T 403/32918
(Continued)

(56) References Cited

U.S. PATENT DOCUMENTS 1,535,312 A 4/1925 Thomas
3,335,719 A 8/1967 Boucher
(Continued)

FOREIGN PATENT DOCUMENTS

DE 9304063 U1 5/1993
DE 19537320 A1 4/1997
(Continued)

OTHER PUBLICATIONS

Alexander, Arthur D. III, "Impacts of Telemation on Modern Society," Symposium on Theory and Practice of Robots and Manipulators, Centre for Mechanical Sciences 1st CISM IFToMM Symposium, Sep. 5-8, 1974, pp. 121-136, vol. 2, Springer-Verlag.
(Continued)

*Primary Examiner* — John P Leubecker

(57) ABSTRACT

A robotic surgical system for performing a procedure within a sterile field comprises a manipulator arm and a surgical accessory clamp for coupling a surgical accessory to a distal end portion of the manipulator arm. The accessory clamp includes a base for coupling with the distal end portion of the manipulator arm, two clamp jaws with each of the clamp jaws directly and rotatably coupled to the base by respective pivot pins, and a lever operable to move the two clamp jaws between an open position and closed position. The system also includes a sterile drape covering the accessory clamp and the manipulator arm to shield the accessory clamp and the manipulator arm from the sterile field.

20 Claims, 28 Drawing Sheets

Related U.S. Application Data continuation-in-part of application No. 10/922,346, filed on Aug. 19, 2004, now Pat. No. 7,357,774, which is a continuation of application No. 10/004,399, filed on Oct. 30, 2001, now abandoned, which is a continuation of application No. 09/406,360, filed on Sep. 28, 1999, now Pat. No. 6,346,072, which is a continuation of application No. 08/975,617, filed on Nov. 21, 1997, now Pat. No. 6,132,368.

(51) Int. Cl.
*F16B 2/10* (2006.01)
*A61B 17/00* (2006.01)

(52) U.S. Cl.
CPC .......... *A61B 34/30* (2016.02); *A61B 46/10* (2016.02); *A61B 90/361* (2016.02); *A61B 2017/00477* (2013.01); *A61B 2034/305* (2016.02); *F16B 2/10* (2013.01); *F16B 2/185* (2013.01)

(58) Field of Classification Search
USPC ..... 600/102, 230; 606/1, 130; 269/236, 196, 269/209, 218; 24/490, 494, 498, 515, 516, 518
See application file for complete search history.

(56) References Cited

U.S. PATENT DOCUMENTS

| | | | |
|---|---|---|---|
| 3,494,356 A | 2/1970 | Frederick | |
| 3,528,720 A | 9/1970 | Treace | |
| 3,622,188 A | 11/1971 | Goeman | |
| 3,645,835 A | 2/1972 | Hodgson | |
| 3,651,536 A | 3/1972 | Bolzan, Jr. et al. | |
| 3,678,933 A | 7/1972 | Moore et al. | |
| 3,698,791 A | 10/1972 | Walchle et al. | |
| 3,707,964 A | 1/1973 | Patience et al. | |
| 3,724,778 A | 4/1973 | Kuhnlein et al. | |
| 3,881,761 A * | 5/1975 | Meyer et al. | 294/198 |
| 3,930,380 A | 1/1976 | Fogt | |
| 3,948,552 A * | 4/1976 | Hamrick | 294/115 |
| 3,951,495 A | 4/1976 | Donaher et al. | |
| 4,038,987 A | 8/1977 | Komiya | |
| 4,045,118 A | 8/1977 | Geraci | |
| 4,099,614 A | 7/1978 | Heissenberger | |
| 4,149,278 A | 4/1979 | Frosch et al. | |
| 4,183,613 A | 1/1980 | Walchle et al. | |
| 4,240,604 A * | 12/1980 | Brach | 248/316.5 |
| 4,245,985 A | 1/1981 | Eibofner et al. | |
| 4,270,367 A | 6/1981 | Santore | |
| 4,281,447 A | 8/1981 | Miller et al. | |
| 4,332,066 A | 6/1982 | Hailey et al. | |
| 4,367,998 A | 1/1983 | Causer | |
| 4,386,933 A | 6/1983 | Sanchez | |
| 4,392,485 A * | 7/1983 | Hiltebrandt | 600/153 |
| 4,456,960 A | 6/1984 | Wakai | |
| 4,457,026 A | 7/1984 | Morris | |
| 4,463,759 A | 8/1984 | Garito et al. | |
| 4,486,928 A | 12/1984 | Tucker et al. | |
| 4,494,712 A | 1/1985 | Godwin, Jr. et al. | |
| 4,500,065 A | 2/1985 | Hennekes et al. | |
| 4,508,280 A | 4/1985 | Hayosh et al. | |
| 4,511,305 A | 4/1985 | Kawai et al. | |
| 4,512,709 A | 4/1985 | Hennekes et al. | |
| 4,561,540 A | 12/1985 | Hunter et al. | |
| 4,573,452 A * | 3/1986 | Greenberg | 600/102 |
| 4,602,623 A | 7/1986 | Cherkassky | |
| 4,647,643 A | 3/1987 | Zdrahala et al. | |
| 4,696,544 A * | 9/1987 | Costella | 385/118 |
| 4,705,038 A | 11/1987 | Sjostrom et al. | |
| 4,706,372 A | 11/1987 | Ferrero et al. | |
| 4,710,093 A | 12/1987 | Zimmer et al. | |
| 4,716,811 A * | 1/1988 | Johnson | 89/40.12 |
| 4,744,363 A | 5/1988 | Hasson | |
| 4,751,925 A | 6/1988 | Tontarra | |
| 4,766,775 A | 8/1988 | Hodge | |
| 4,793,053 A | 12/1988 | Zuccaro et al. | |
| 4,799,779 A | 1/1989 | Mesmer | |
| 4,809,747 A | 3/1989 | Choly et al. | |
| 4,830,569 A | 5/1989 | Jannborg | |
| 4,832,198 A | 5/1989 | Alikhan | |
| 4,834,090 A | 5/1989 | Moore | |
| 4,837,703 A | 6/1989 | Kakazu et al. | |
| 4,848,758 A * | 7/1989 | Mills | 269/16 |
| 4,863,204 A * | 9/1989 | Peters | 294/115 |
| 4,905,710 A | 3/1990 | Jones | |
| 4,915,563 A | 4/1990 | Teillauchet et al. | |
| 4,919,112 A | 4/1990 | Siegmund | |
| 4,928,546 A | 5/1990 | Walters | |
| 4,943,939 A | 7/1990 | Hoover | |
| 4,979,949 A | 12/1990 | Matsen, III | |
| 4,980,963 A | 1/1991 | Dinse | |
| 4,996,975 A | 3/1991 | Nakamura | |
| 5,018,266 A | 5/1991 | Hutchinson et al. | |
| 5,051,000 A | 9/1991 | Cadwallader et al. | |
| 5,052,396 A | 10/1991 | Wedel et al. | |
| 5,052,402 A | 10/1991 | Bencini et al. | |
| 5,055,660 A * | 10/1991 | Bertagna et al. | 235/472.02 |
| 5,077,506 A | 12/1991 | Krause | |
| 5,078,140 A | 1/1992 | Kwoh | |
| 5,080,108 A | 1/1992 | Roth | |
| 5,086,401 A | 2/1992 | Glassman et al. | |
| 5,122,904 A | 6/1992 | Fujiwara et al. | |
| 5,133,735 A | 7/1992 | Slater et al. | |
| 5,143,453 A | 9/1992 | Weynant nee Girones | |
| 5,154,717 A | 10/1992 | Matsen, III et al. | |
| 5,155,693 A | 10/1992 | Altmayer et al. | |
| 5,174,300 A | 12/1992 | Bales et al. | |
| 5,176,702 A | 1/1993 | Bales et al. | |
| 5,184,601 A | 2/1993 | Putman | |
| 5,207,213 A * | 5/1993 | Auhll et al. | 600/104 |
| 5,217,003 A | 6/1993 | Wilk | |
| 5,221,283 A | 6/1993 | Chang | |
| 5,236,432 A | 8/1993 | Matsen, III et al. | |
| 5,243,266 A | 9/1993 | Kasagami et al. | |
| 5,251,127 A * | 10/1993 | Raab | 606/130 |
| 5,255,429 A | 10/1993 | Nishi et al. | |
| 5,257,998 A | 11/1993 | Ota et al. | |
| 5,259,690 A * | 11/1993 | Legge | 403/385 |
| 5,271,384 A | 12/1993 | McEwen et al. | |
| 5,274,500 A | 12/1993 | Dunn | |
| 5,275,608 A | 1/1994 | Forman et al. | |
| 5,284,487 A | 2/1994 | Hartmeister | |
| 5,294,209 A | 3/1994 | Naka et al. | |
| 5,295,933 A * | 3/1994 | Ciminski | A63B 21/0728 24/270 |
| 5,305,203 A | 4/1994 | Raab | |
| 5,312,212 A | 5/1994 | Naumec | |
| 5,313,935 A | 5/1994 | Kortenbach et al. | |
| 5,316,541 A | 5/1994 | Fischer | |
| 5,318,589 A | 6/1994 | Lichtman | |
| 5,337,732 A | 8/1994 | Grundfest et al. | |
| 5,339,799 A | 8/1994 | Kami et al. | |
| 5,343,385 A | 8/1994 | Joskowicz et al. | |
| 5,354,296 A | 10/1994 | Turkel | |
| 5,354,314 A | 10/1994 | Hardy et al. | |
| 5,355,743 A | 10/1994 | Tesar | |
| 5,359,993 A | 11/1994 | Slater et al. | |
| 5,369,851 A * | 12/1994 | Merkel | 24/136 R |
| 5,372,147 A | 12/1994 | Lathrop, Jr. et al. | |
| 5,380,338 A * | 1/1995 | Christian | 606/130 |
| 5,382,885 A | 1/1995 | Salcudean et al. | |
| 5,397,323 A | 3/1995 | Taylor et al. | |
| 5,399,951 A | 3/1995 | Lavallee et al. | |
| 5,400,267 A | 3/1995 | Denen et al. | |
| 5,400,772 A | 3/1995 | LeVahn et al. | |
| 5,402,793 A | 4/1995 | Gruner et al. | |
| 5,402,801 A | 4/1995 | Taylor | |
| 5,403,319 A | 4/1995 | Matsen, III et al. | |
| 5,413,573 A | 5/1995 | Koivukangas | |
| 5,417,210 A | 5/1995 | Funda et al. | |
| 5,427,097 A | 6/1995 | Depp | |

(56) References Cited

U.S. PATENT DOCUMENTS

| | | |
|---|---|---|
| 5,429,142 A | 7/1995 | Szabo et al. |
| 5,433,221 A | 7/1995 | Adair |
| 5,441,042 A | 8/1995 | Putman |
| 5,445,638 A | 8/1995 | Rydell et al. |
| 5,451,368 A | 9/1995 | Jacob |
| 5,457,857 A * | 10/1995 | Lam .................. 24/503 |
| 5,458,132 A | 10/1995 | Yabe et al. |
| 5,480,409 A | 1/1996 | Riza |
| 5,490,524 A | 2/1996 | Williams et al. |
| 5,498,230 A | 3/1996 | Adair |
| 5,520,678 A | 5/1996 | Heckele et al. |
| 5,535,973 A | 7/1996 | Bailey et al. |
| 5,562,700 A | 10/1996 | Huitema et al. |
| 5,570,500 A * | 11/1996 | Merkel .................. 24/495 |
| 5,571,110 A | 11/1996 | Matsen, III et al. |
| 5,617,857 A | 4/1997 | Chader et al. |
| 5,624,398 A | 4/1997 | Smith et al. |
| 5,630,431 A | 5/1997 | Taylor |
| 5,631,832 A | 5/1997 | Hagenbuch |
| 5,631,973 A | 5/1997 | Green |
| 5,649,956 A | 7/1997 | Jensen et al. |
| 5,658,077 A | 8/1997 | Hoftman |
| 5,676,673 A | 10/1997 | Ferre et al. |
| 5,678,284 A * | 10/1997 | Genero et al. .................. 24/327 |
| 5,690,635 A | 11/1997 | Matsen, III et al. |
| 5,695,500 A | 12/1997 | Taylor et al. |
| 5,695,501 A | 12/1997 | Carol et al. |
| 5,697,939 A | 12/1997 | Kubota et al. |
| 5,710,870 A | 1/1998 | Ohm et al. |
| 5,716,354 A | 2/1998 | Hluchy |
| 5,732,712 A | 3/1998 | Adair |
| 5,741,210 A | 4/1998 | Dobrovolny |
| 5,749,885 A | 5/1998 | Sjostrom et al. |
| 5,762,458 A | 6/1998 | Wang et al. |
| 5,765,565 A | 6/1998 | Adair |
| 5,779,623 A * | 7/1998 | Bonnell .................. 600/114 |
| 5,784,542 A | 7/1998 | Ohm et al. |
| 5,785,643 A | 7/1998 | Lynn |
| 5,792,044 A * | 8/1998 | Foley et al. .................. 600/114 |
| 5,792,135 A | 8/1998 | Madhani et al. |
| 5,797,900 A | 8/1998 | Madhani et al. |
| 5,800,423 A | 9/1998 | Jensen |
| 5,802,641 A | 9/1998 | Van Steenburg |
| 5,807,377 A | 9/1998 | Madhani et al. |
| 5,807,378 A | 9/1998 | Jensen et al. |
| 5,808,665 A | 9/1998 | Green |
| 5,810,880 A | 9/1998 | Jensen et al. |
| 5,814,038 A | 9/1998 | Jensen et al. |
| 5,817,084 A | 10/1998 | Jensen |
| 5,830,121 A | 11/1998 | Enomoto et al. |
| 5,833,656 A | 11/1998 | Smith et al. |
| 5,849,022 A | 12/1998 | Sakashita et al. |
| 5,853,363 A | 12/1998 | Vought |
| 5,855,583 A | 1/1999 | Wang et al. |
| 5,873,814 A | 2/1999 | Adair |
| 5,876,325 A | 3/1999 | Mizuno et al. |
| 5,876,328 A | 3/1999 | Fox et al. |
| 5,878,193 A | 3/1999 | Wang et al. |
| 5,929,899 A | 7/1999 | Takahashi et al. |
| 5,931,832 A | 8/1999 | Jensen |
| 5,941,889 A | 8/1999 | Cermak |
| 5,951,461 A | 9/1999 | Nyo et al. |
| 5,954,259 A | 9/1999 | Viola et al. |
| 5,957,831 A | 9/1999 | Adair |
| 5,964,780 A | 10/1999 | Balazs |
| 5,970,980 A | 10/1999 | Adair |
| 5,971,997 A | 10/1999 | Guthrie et al. |
| 5,976,122 A | 11/1999 | Madhani et al. |
| 5,992,782 A | 11/1999 | Goodknight |
| 5,996,889 A * | 12/1999 | Fuchs et al. .................. 235/375 |
| 5,997,471 A | 12/1999 | Gumb et al. |
| 6,024,695 A | 2/2000 | Taylor et al. |
| 6,042,166 A * | 3/2000 | Conte .................. 294/202 |
| 6,056,281 A * | 5/2000 | Moilanen et al. .................. 269/32 |
| 6,063,095 A | 5/2000 | Wang et al. |
| 6,067,869 A | 5/2000 | Chilla et al. |
| 6,102,044 A | 8/2000 | Naidyhorski |
| 6,102,850 A | 8/2000 | Wang et al. |
| 6,120,433 A | 9/2000 | Mizuno et al. |
| 6,123,080 A | 9/2000 | Mohan et al. |
| 6,132,368 A | 10/2000 | Cooper |
| 6,134,993 A | 10/2000 | Tally |
| 6,149,607 A | 11/2000 | Simpson et al. |
| 6,151,981 A | 11/2000 | Costa |
| 6,152,871 A * | 11/2000 | Foley et al. .................. 600/114 |
| 6,152,920 A | 11/2000 | Thompson et al. |
| 6,167,658 B1 | 1/2001 | Weiner |
| 6,167,884 B1 | 1/2001 | Navis |
| 6,190,399 B1 | 2/2001 | Palmer et al. |
| D438,617 S | 3/2001 | Cooper et al. |
| 6,197,017 B1 | 3/2001 | Brock et al. |
| 6,206,903 B1 | 3/2001 | Ramans |
| 6,208,515 B1 | 3/2001 | Klein |
| D441,076 S | 4/2001 | Cooper et al. |
| D441,862 S | 5/2001 | Cooper et al. |
| 6,231,565 B1 | 5/2001 | Tovey et al. |
| 6,236,880 B1 | 5/2001 | Raylman et al. |
| 6,246,200 B1 | 6/2001 | Blumenkranz et al. |
| D444,555 S | 7/2001 | Cooper et al. |
| 6,259,806 B1 | 7/2001 | Green |
| 6,276,312 B1 | 8/2001 | Summan et al. |
| 6,325,808 B1 | 12/2001 | Bernard et al. |
| 6,327,756 B1 * | 12/2001 | Maziere .................. 24/495 |
| 6,331,181 B1 | 12/2001 | Tierney et al. |
| 6,334,860 B1 | 1/2002 | Dorn |
| 6,346,072 B1 | 2/2002 | Cooper |
| 6,370,411 B1 | 4/2002 | Osadchy et al. |
| 6,394,998 B1 | 5/2002 | Wallace et al. |
| 6,398,726 B1 | 6/2002 | Ramans et al. |
| 6,424,885 B1 | 7/2002 | Niemeyer et al. |
| 6,434,507 B1 | 8/2002 | Clayton et al. |
| 6,451,027 B1 | 9/2002 | Cooper et al. |
| 6,468,265 B1 | 10/2002 | Evans et al. |
| 6,491,701 B2 | 12/2002 | Tierney |
| 6,554,844 B2 | 4/2003 | Lee et al. |
| 6,607,170 B1 | 8/2003 | Hoftman |
| 6,612,310 B2 | 9/2003 | Sklar |
| 6,676,684 B1 | 1/2004 | Morley et al. |
| 6,699,177 B1 | 3/2004 | Laby et al. |
| 6,738,656 B1 | 5/2004 | Ferre et al. |
| 6,770,081 B1 | 8/2004 | Cooper |
| 6,805,453 B2 | 10/2004 | Spetzler et al. |
| 6,862,780 B2 * | 3/2005 | Henry .................. A47F 5/0884 211/48 |
| 6,866,671 B2 | 3/2005 | Tierney et al. |
| 6,889,116 B2 | 5/2005 | Jinno |
| 6,912,959 B2 | 7/2005 | Kolody et al. |
| 6,936,042 B2 | 8/2005 | Wallace et al. |
| 6,966,104 B2 * | 11/2005 | Gregel et al. .................. 29/280 |
| 7,048,745 B2 | 5/2006 | Tierney et al. |
| 7,074,180 B2 | 7/2006 | Bertolero et al. |
| 7,122,032 B2 | 10/2006 | Shinmura et al. |
| 7,250,028 B2 | 7/2007 | Julian et al. |
| 7,263,501 B2 * | 8/2007 | Tirinato et al. .................. 705/28 |
| 7,320,556 B2 | 1/2008 | Vagn-Erik |
| 7,357,774 B2 | 4/2008 | Cooper |
| 7,395,563 B2 * | 7/2008 | Whitmore et al. .................. 5/601 |
| 7,524,320 B2 | 4/2009 | Tierney et al. |
| 7,666,191 B2 | 2/2010 | Orban, III et al. |
| 7,699,855 B2 | 4/2010 | Anderson et al. |
| 7,727,244 B2 | 6/2010 | Orban, III et al. |
| 7,770,859 B2 * | 8/2010 | Costabel et al. .................. 248/316.5 |
| 7,819,885 B2 | 10/2010 | Cooper |
| 7,907,166 B2 | 3/2011 | Lamprecht et al. |
| 7,918,861 B2 | 4/2011 | Brock et al. |
| 7,963,913 B2 | 6/2011 | Devengenzo et al. |
| 8,105,338 B2 | 1/2012 | Anderson et al. |
| 8,142,447 B2 | 3/2012 | Cooper et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,216,250 B2 | 7/2012 | Orban, III et al. |
| 8,529,582 B2 | 9/2013 | Devengenzo et al. |
| 8,608,773 B2 | 12/2013 | Tierney et al. |

(56) References Cited

U.S. PATENT DOCUMENTS

| | | | |
|---|---|---|---|
| 8,758,352 B2 | 6/2014 | Cooper et al. |
| 8,998,799 B2 | 4/2015 | Orban, III et al. |
| 8,998,930 B2 | 4/2015 | Orban, III |
| 2002/0045888 A1 | 4/2002 | Ramans et al. |
| 2002/0087048 A1 | 7/2002 | Brock et al. |
| 2002/0091374 A1 | 7/2002 | Cooper |
| 2002/0177754 A1* | 11/2002 | Phillips ................. 600/234 |
| 2003/0006653 A1 | 1/2003 | Kang et al. |
| 2003/0050649 A1 | 3/2003 | Brock et al. |
| 2003/0085147 A1 | 5/2003 | Gabriele |
| 2003/0111366 A1 | 6/2003 | Enners |
| 2004/0035334 A1 | 2/2004 | Lohrengel et al. |
| 2004/0049205 A1 | 3/2004 | Lee et al. |
| 2004/0127891 A1 | 7/2004 | Humble et al. |
| 2004/0133189 A1 | 7/2004 | Sakurai |
| 2004/0179754 A1 | 9/2004 | Taheri |
| 2005/0021050 A1 | 1/2005 | Cooper |
| 2005/0051050 A1 | 3/2005 | Bindra |
| 2005/0149003 A1 | 7/2005 | Tierney et al. |
| 2005/0184207 A1 | 8/2005 | Bertram |
| 2005/0222554 A1 | 10/2005 | Wallace et al. |
| 2005/0240178 A1 | 10/2005 | Morley et al. |
| 2006/0111692 A1* | 5/2006 | Hlavka et al. ............. 604/890.1 |
| 2006/0161136 A1 | 7/2006 | Anderson et al. |
| 2006/0167440 A1 | 7/2006 | Cooper et al. |
| 2006/0276775 A1 | 12/2006 | Rosenberg et al. |
| 2007/0043338 A1 | 2/2007 | Moll et al. |
| 2007/0070157 A1 | 3/2007 | Wang |
| 2007/0137371 A1 | 6/2007 | Devengenzo et al. |
| 2007/0137372 A1 | 6/2007 | Devengenzo et al. |
| 2007/0142824 A1 | 6/2007 | Devengenzo et al. |
| 2007/0142969 A1 | 6/2007 | Devengenzo et al. |
| 2007/0185376 A1 | 8/2007 | Wilson et al. |
| 2007/0239172 A1 | 10/2007 | Lee et al. |
| 2009/0030429 A1 | 1/2009 | Madhani et al. |
| 2009/0247819 A1 | 10/2009 | Wilson et al. |
| 2011/0028990 A1 | 2/2011 | Cooper |
| 2011/0066161 A1 | 3/2011 | Cooper |
| 2012/0232566 A1 | 9/2012 | Orban, III et al. |
| 2012/0239060 A1 | 9/2012 | Orban, III |
| 2012/0247489 A1 | 10/2012 | Orban, III et al. |
| 2013/0331858 A1 | 12/2013 | Devengenzo et al. |
| 2014/0180310 A1 | 6/2014 | Blumenkranz et al. |
| 2015/0173841 A1 | 6/2015 | Orban, III |

FOREIGN PATENT DOCUMENTS

| | | |
|---|---|---|
| DE | 19950440 A1 | 11/2001 |
| DE | 102007030856 B3 | 4/2009 |
| EP | 0606531 A2 | 7/1994 |
| EP | 0705571 A1 | 4/1996 |
| EP | 1321106 A1 | 6/2003 |
| EP | 1439026 A1 | 7/2004 |
| EP | 1889576 A2 | 2/2008 |
| EP | 2263594 A2 | 12/2010 |
| EP | 2263595 A2 | 12/2010 |
| GB | 2366319 | 3/2002 |
| JP | S59190214 U | 12/1984 |
| JP | H01280449 A | 11/1989 |
| JP | H03121064 A | 5/1991 |
| JP | H03143438 A | 6/1991 |
| JP | 4092656 A | 3/1992 |
| JP | H0661205 U | 8/1994 |
| JP | H06261911 A | 9/1994 |
| JP | H06269461 A | 9/1994 |
| JP | 7-194610 | 8/1995 |
| JP | H07241300 A | 9/1995 |
| JP | H07509637 A | 10/1995 |
| JP | H0884735 A | 4/1996 |
| JP | 8182684 A | 7/1996 |
| JP | H08215211 A | 8/1996 |
| JP | H08224248 A | 9/1996 |
| JP | H08280697 A | 10/1996 |
| JP | H08509886 A | 10/1996 |
| JP | H11507252 A | 6/1999 |
| JP | 2000505328 A | 5/2000 |
| JP | 2002500524 A | 1/2002 |
| JP | 2003061969 | 3/2003 |
| JP | 2003235868 A | 8/2003 |
| JP | 2003325543 A | 11/2003 |
| JP | 2004-000334 | 1/2004 |
| JP | 2004097533 A | 4/2004 |
| JP | 2004244091 A | 9/2004 |
| JP | 2005524442 A | 8/2005 |
| WO | WO-9220295 | 11/1992 |
| WO | WO9313916 | 7/1993 |
| WO | WO-9320770 A2 | 10/1993 |
| WO | WO-9403113 A1 | 2/1994 |
| WO | WO-9414129 A1 | 6/1994 |
| WO | WO9426167 | 11/1994 |
| WO | WO-9503001 A1 | 2/1995 |
| WO | WO-9505780 A1 | 3/1995 |
| WO | WO9516396 | 6/1995 |
| WO | WO9530964 | 11/1995 |
| WO | WO-9608209 A2 | 3/1996 |
| WO | WO9639944 | 12/1996 |
| WO | WO-9712554 A1 | 4/1997 |
| WO | WO-9728734 A1 | 8/1997 |
| WO | WO-9729690 A1 | 8/1997 |
| WO | WO-9729710 A1 | 8/1997 |
| WO | WO 199825666 | 6/1998 |
| WO | WO-9950721 A1 | 10/1999 |
| WO | WO-0001304 A1 | 1/2000 |
| WO | WO-0033755 A1 | 6/2000 |
| WO | WO-03092523 A1 | 11/2003 |

OTHER PUBLICATIONS

International Search Report for application No. PCT/US97/22035, Mailed on Apr. 21, 1998, 2 pages.
Co-pending U.S. Appl. No. 60/033,321, filed Dec. 12. 1996.
Co-pending U.S Appl. No. 60/752,472, filed Dec. 20, 2005.
Co-pending U.S. Appl. No. 60/752,755, filed Dec. 20, 2005.
Co-pending U.S. Appl. No. 60/986,914, filed Nov. 9, 2007.
European Search Report for Application No. EP09172358, mailed on Jan. 17, 2012, 6 pages.
European Search Report for Application No. EP10182919, mailed on Feb. 14, 2013, 9 pages.
European Search Report for Application No. EP10182920, mailed on Feb. 11, 2013, 5 pages.
European Search Report for Application No. EP10182921 mailed on Mar. 7, 2013, 7 pages.
Extended European Search Report for Application No. EP10182922 mailed on Feb. 6, 2013, 7 pages.
Extended European Search Report for Application No. EP11156882, mailed on May 19, 2011, 7 pages.
Extended European Search Report for Application No. EP12192481, mailed on Nov. 13, 2013, 8 pages.
FR0611140 Preliminary Search Report Notification and Written Opinion, dated Aug. 4, 2009, 5 pages.
FR0611141 Preliminary Search Report Notification and Written Opinion, dated Aug. 4, 2009, 5 pages.
French Preliminary Search Report for Application No. 1255442, mailed on Feb. 8, 2013, 12 pages.
Green P.S., et al., "Telepresence Surgery," IEEE Engineering in Medicine and Biology Magazine, IEEE Sevice Center, Pisacataway, NJ, US, May 1, 1995, vol. 14 (3), pp. 324-329, XP000505090.
International Search Report and Written Opinion for Application No. PCT/US2008/082628, mailed Jun. 16, 2009, 9 pages.
JP 2008-547535 Office Action dated Dec. 19, 2011, 7 pages.
PCT/US06/37432 International Search Report, mailed Dec. 15, 2006, 4 pages.
PCT/US06/37432 Written Opinion of the International Search Authority, mailed Dec. 15, 2006, 7 pages.
PCT/US06/48744 International Search Report and Written Opinion of the International Searching Authority, mailed May 8, 2007, 11 pages.
PCT/US06/62363 International Search Report, mailed Dec. 14, 2007, 2 pages.

(56) References Cited

OTHER PUBLICATIONS

PCT/US06/62363 Written Opinion of the International Search Authority, mailed Dec. 14, 2007, 5 pages.
PCT/US06/62364 International Search Report, mailed Jun. 12, 2006, 3 pages.
PCT/US06/62364 Written Opinion of the International Search Authority, mailed Jun. 12, 2006, 4 pages.
Sabatini, A. M. et al., "Force Feedback Based Telemicromanipulation for Robot Surgery on Soft Tissue," IEEE Engineering in Medicine and Biology Society 11th Annual International Conference, 1989, pp. 890-891, vol. 3, IEEE.
Supplementary European Search Report for Application No. EP97949717, mailed on Mar. 7, 2008, 3 pages.
Vertut, Jean, and Coeffet, Philippe Coiffet; Robot Technology; vol. 3A Teleoperation and Robotics Evolution and Development; 1986; Prentice-Hall, Inc. Englewood Cliffs, NJ.
International Search Report and Written Opinion of the International Searching Authority for PCT/US2006/37434, mailed Feb. 19, 2007, 12 pages.
Green, Philip, U.S. Appl. No. 08/517,053, filed Aug. 21, 1995, Abandoned May 27, 1998.
Extended European Search Report for Application No. EP10182603, mailed on Sep. 23, 2014, 17 pages.
Extended European Search Report for Application No. EP10182720, mailed on Sep. 23, 2014, 15 pages.
EP11155101.6 European Search Report, mailed May 26, 2011, 7 pages.
EP11156085.0 European Search Report, mailed May 31, 2011, 7 pages.
European Search Report for Application No. EP11156082, mailed Jul. 1, 2011, 11 pages.
European Search Report for Application No. EP11156083, mailed on Feb. 28, 2012, 8 pages.
European Search Report for Application No. EP11156087, mailed on Jun. 21, 2011, 9 pages.
European Search Report for Application No. EP11156090, mailed on Jun. 21, 2011, 12 pages.
European Search Report for Application No. EP11156097, mailed on Jul. 18, 2011, 10 pages.
Extended European Search Report for Application No. EP09172378, mailed on Jul. 27, 2010, 10 pages.
International Search Report for application No. PCT/US99/29045, Mailed on May 9, 2000, 1 page.
Madhani, Akhil J. et al., "The black falcon: A teleoperated surgical instrument for minimally invasive surgery," IEEE/RSJ Int. Conf. on Intelligent Robots and Systems (IROS) Victoria B.C. Canada ), 1998, pp. 936-944, vol. 2, IEEE.
Moyer, Thomas H., "The design for an integrated hand and wrist mechanism," Masters Thesis, Feb. 1992, 106 pages, Massachusetts Institute of Technology.
Neisius B. et al., "Robotic manipulator for endoscopic handling of surgical effectors and cameras," 1st Intl. Symposium on Medical Robotics and Computer Assisted Surgery, 1994, pp. 169-176, vol. 2.
Partial European Search Report for Application No. EP07119840, mailed on Jun. 23, 2008, 17 pages.
Partial European Search Report for Application No. EP10182603, mailed on Apr. 18, 2012, 9 pages.
Partial European Search Report for Application No. EP10182720, mailed on Apr. 20, 2012, 6 pages.
Partial European Search Report for Application No. EP10182750, mailed on May 11, 2012, 10 pages.
Partial European Search Report for Application No. EP10182798, mailed on May 4, 2012, 9 pages.
Salisbury, Kenneth J., "Kinematic and force analysis of articulated hands," Department of Computer Science Stanford University Report No. STAN CS 89 921, 1982, Chapter 9, pp. 67-77.
Supplementary European Search Report for Application No. EP99968468, mailed on Aug. 13, 2004, 6 pages.
TASK 2: Miniature end effector—A preliminary design, pp. 32-47, no date.
Thring, M.W., Robots and Telechirs: Manipulators with Memory; Remote Manipulators; Machine Limbs for the Handicapped, 1983, pp. 9-11, 108-131, 194-195, 235-279; Ellis Horwood Limited, Chapter 5,7,8,9.
Office Action mailed Oct. 24, 2014 for Japanese Application No. 2013231856 filed Nov. 8, 2013, 5 pages.
Extended European Search Report for Application No. 15174908.2, mailed on Dec. 7, 2015, 5 pages.
Office Action mailed Mar. 29, 2016 for Japanese Application No. 2014-179860 filed Sep. 4, 2014, 10 pages.
Supplementary Partial European Search Report for Application No. 20100182798, mailed on Mar. 20, 2015, 5 pages.
Office Action mailed Jun. 4, 2014 for Japanese Application No. 20120219670 filed Oct. 1, 2012, 8 pages.

* cited by examiner

SURGICAL ACCESSORY CLAMP AND SYSTEM

CROSS-REFERENCE TO RELATED APPLICATIONS

This application is a divisional of U.S. patent application Ser. No. 11/240,087, filed Sep. 30, 2005, now U.S. Pat. No. 8,182,469, which is a continuation-in-part of U.S. patent application Ser. No. 10/922,346, filed Aug. 19, 2004, now U.S. Pat. No. 7,357,774, which is a continuation of U.S. patent application Ser. No. 10/004,399, filed Oct. 30, 2001, now abandoned, which is a continuation of U.S. patent application Ser. No. 09/406,360, filed Sep. 28, 1999, now U.S. Pat. No. 6,346,072, which is a continuation of U.S. patent application Ser. No. 08/975,617, filed Nov. 21, 1997, now U.S. Pat. No. 6,132,368, the full disclosures of which are hereby incorporated by reference for all purposes.

TECHNICAL FIELD

The present invention relates generally to surgical robot systems and, more particularly, to accessory clamps for robotic arms.

BACKGROUND

In robotically-assisted or telerobotic surgery, the surgeon typically operates a master controller to remotely control the motion of surgical instruments at the surgical site from a location that may be remote from the patient (e.g., across the operating room, in a different room or a completely different building from the patient). The master controller usually includes one or more hand input devices, such as joysticks, exoskeletal gloves or the like, which are coupled to the surgical instruments with servo motors for articulating the instruments at the surgical site. The servo motors are typically part of an electromechanical device or surgical manipulator ("the slave") that supports and controls the surgical instruments that have been introduced directly into an open surgical site or through trocar sleeves into a body cavity, such as the patient's abdomen. During the operation, the surgical manipulator provides mechanical articulation and control of a variety of surgical instruments, such as tissue graspers, needle drivers, electrosurgical cautery probes, etc., that each perform various functions for the surgeon, e.g., holding or driving a needle, grasping a blood vessel, or dissecting, cauterizing or coagulating tissue.

This new method of performing telerobotic surgery through remote manipulation has, of course, created many new challenges. One such challenge results from the fact that a portion of the electromechanical surgical manipulator will be in direct contact with the surgical instruments, and will also be positioned adjacent the operation site. Accordingly, the surgical manipulator may become contaminated during surgery and is typically disposed of or sterilized between operations. From a cost perspective, it would be preferable to sterilize the device. However, the servo motors, sensors, encoders, and electrical connections that are necessary to robotically control the motors typically cannot be sterilized using conventional methods, e.g., steam, heat and pressure, or chemicals, because the system parts would be damaged or destroyed in the sterilization process.

Yet another challenge with telerobotic surgery systems is that a surgeon will typically employ a large number of different surgical instruments during a procedure. Since the number of instrument holders are limited due to space constraints and cost, many of these surgical instruments will be attached and detached from the same instrument holder a number of times during an operation. In laparoscopic procedures, for example, the number of entry ports into the patient's abdomen is generally limited during the operation because of space constraints as well as a desire to avoid unnecessary incisions in the patient. Thus, a number of different surgical instruments will typically be introduced through the same trocar sleeve during the operation. Likewise, in open surgery, there is typically not enough room around the surgical site to position more than one or two surgical manipulators, and so the surgeon's assistant will be compelled to frequently remove instruments from the holder and exchange them with other surgical tools. However in the past, instrument holders have been difficult or cumbersome to use, requiring the use of both hands. Furthermore, past instrument holders have been required to be detached and sterilized after each procedure.

What is needed, therefore, are improved telerobotic systems and methods for remotely controlling surgical instruments at a surgical site on a patient. These systems and methods should be configured to minimize the need for sterilization to improve cost efficiency. In addition, these systems and methods should be designed to minimize instrument exchange time and difficulty during the surgical procedure. Accordingly, an accessory clamp and system for robotic surgery having improved efficiency and cost-effectiveness is highly desirable.

SUMMARY

The present invention provides an advantageous system, apparatus, and method for clamping of surgical accessories used for telerobotic surgery.

In accordance with an embodiment of the present invention, a surgical accessory clamp of a robotic surgical system is provided, the accessory clamp including a base for coupling to a distal end of a manipulator arm, and two clamp jaws for receiving a surgical accessory, the two clamp jaws operably coupled to the base. The clamp further includes a sterile drape portion over the two clamp jaws, and a lever portion capable of actuating the two clamp jaws into an open position or a closed position.

In accordance with another embodiment of the present invention, a surgical accessory clamp of a robotic surgical system is provided, the accessory clamp including a base for coupling to a distal end of a manipulator arm, the base including a first mounting portion; a sterile drape portion over the first mounting portion; and a second mounting portion for clamping or releasing a surgical accessory between the first and second mounting portions.

In accordance with yet another embodiment of the present invention, a robotic surgical system for performing a procedure within a sterile field is provided, the system including a manipulator arm, a surgical accessory clamp for coupling a surgical accessory to a distal end portion of the manipulator arm, and a sterile drape covering the accessory clamp and the manipulator arm to shield the accessory clamp and the manipulator arm from the sterile field.

In accordance with yet another embodiment of the present invention, a robotic surgical system for performing a procedure within a sterile field is provided, the system including a surgical tool; a manipulator assembly including a manipulator arm having proximal and distal end portions; a cannula defining an inner lumen for receiving the surgical tool and providing access through a percutaneous penetration in the patient; a cannula adaptor for coupling the cannula to the distal end portion of the manipulator arm; and a sterile drape covering the cannula adaptor and the manipulator arm to shield the cannula adaptor and the manipulator arm from the sterile field.

In accordance with yet another embodiment of the present invention, a method of clamping a surgical accessory in a robotic surgical system is provided, the method including providing a surgical accessory clamp as described above, positioning a sterile drape over the two clamp jaws, actuating the accessory clamp into the open position, providing the surgical accessory between the two clamp jaws, and actuating the accessory clamp into the closed position.

In accordance with yet another embodiment of the present invention, a method of clamping a surgical accessory in a robotic surgical system is provided, the method including attaching a surgical accessory clamp to a distal end portion of a manipulator arm, covering the manipulator arm and accessory clamp with a sterile drape to shield the manipulator arm and accessory clamp from a sterile field, and attaching an accessory to the accessory clamp within the sterile field.

Advantageously, the present invention provides an enhanced clamping apparatus and method for robotic surgical systems that does not require re-sterilization and allows for easy exchange of instruments, tools, or accessories, thereby improving cost-effectiveness and efficiency.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

Figure 1:
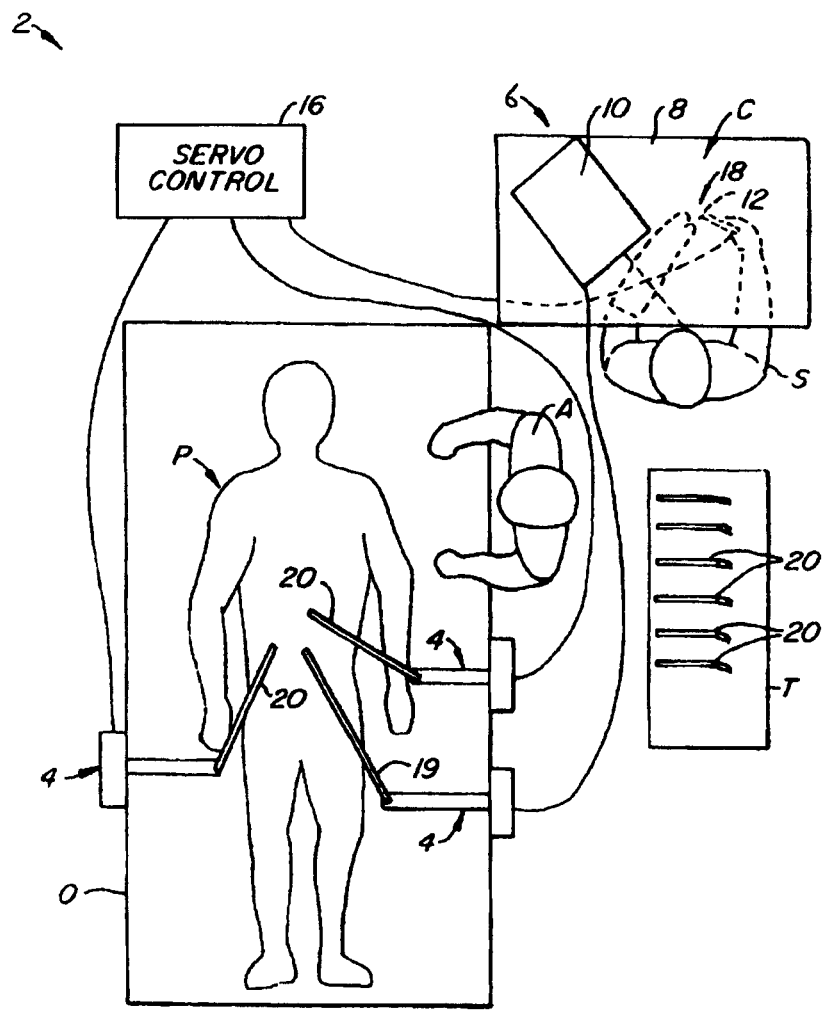
FIG. 1 is a schematic view of an operating room, illustrating a telerobotic surgical system and method in accordance with an embodiment of the present invention.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention provides a multi-component system and method for performing robotically-assisted surgical procedures on a patient, particularly including open surgical procedures, neurosurgical procedures, such as stereotaxy, and endoscopic procedures, such as laparoscopy, arthroscopy, thoracoscopy and the like. The system and method of the present invention is particularly useful as part of a telerobotic surgical system that allows the surgeon to manipulate the surgical instruments through a servomechanism from a remote location from the patient. To that end, the manipulator apparatus or slave of the present invention will usually be driven by a kinematically-equivalent master to form a telepresence system with force reflection. A description of a suitable slave-master system can be found in U.S. patent application Ser. No. 08/517,053, filed Aug. 21, 1995, the complete disclosure of which is incorporated herein by reference for all purposes.

Referring to the drawings in detail, wherein like numerals indicate like elements, a telerobotic surgical system 2 is illustrated according to an embodiment of the present invention. As shown in FIG. 1, telerobotic system 2 generally includes one or more surgical manipulator assemblies 4 mounted to or near an operating table O, and a control assembly 6 for allowing the surgeon S to view the surgical site and to control the manipulator assemblies 4. The system 2 will also include one or more viewing scope assemblies 19 and a plurality of surgical instrument assemblies 20 adapted for being removably coupled to manipulator assemblies 4 (discussed in detail below). Telerobotic system 2 usually includes at least two manipulator assemblies 4 and preferably three manipulator assemblies 4. The exact number of manipulator assemblies 4 will depend on the surgical procedure and the space constraints within the operating room among other factors. As discussed in detail below, one of the assemblies 4 will typically operate a viewing scope assembly 19 (e.g., in endoscopic procedures) for viewing the surgical site, while the other manipulator assemblies 4 operate surgical instruments 20 for performing various procedures on the patient P.

Control assembly 6 may be located at a surgeon's console C which is usually located in the same room as operating table O so that the surgeon may speak to his/her assistant(s) A and directly monitor the operating procedure. However, it should be understood that the surgeon S can be located in a different room or a completely different building from the patient P. Control assembly 6 generally includes a support 8, a monitor 10 for displaying an image of the surgical site to the surgeon S, and one or more controller(s) 12 for controlling manipulator assemblies 4. Controller(s) 12 may include a variety of input devices, such as joysticks, gloves, trigger-guns, hand-operated controllers, voice recognition devices or the like. Preferably, controller(s) 12 will be provided with the same degrees of freedom as the associated surgical instrument assemblies 20 to provide the surgeon with telepresence, or the perception that the controller(s) 12 are integral with the instruments 20 so that the surgeon has a strong sense of directly controlling instruments 20. Position, force, and tactile feedback sensors (not shown) may also be employed on instrument assemblies 20 to transmit position, force, and tactile sensations from the surgical instrument back to the surgeon's hands as he/she operates the telerobotic system. One suitable system and method for providing telepresence to the operator is described in U.S. patent application Ser. No. 08/517,053, filed Aug. 21, 1995, which has previously been incorporated herein by reference.

Monitor 10 will be suitably coupled to the viewing scope assembly 19 such that an image of the surgical site is provided adjacent the surgeon's hands on surgeon console C. Preferably, monitor 10 will display an inverted image on a display 18 that is oriented so that the surgeon feels that he or she is actually looking directly down onto the operating site. To that end, an image of the surgical instruments 20 appears to be located substantially where the operator's hands are located even though the observation points (i.e., the endoscope or viewing camera) may not be from the point of view of the image. In addition, the real-time image is preferably transformed into a perspective image such that the operator can manipulate the end effector and the hand control as if viewing the workspace in substantially true presence. By true presence, it is meant that the presentation of an image is a true perspective image simulating the viewpoint of an operator that is physically manipulating the surgical instruments 20. Thus, a controller (not shown) transforms the coordinates of the surgical instruments 20 to a perceived position so that the perspective image is the image that one would see if the camera or endoscope was located directly behind the surgical instruments 20. A suitable coordinate transformation system for providing this virtual image is described in U.S. patent application Ser. No. 08/239,086, filed May 5, 1994, now U.S. Pat. No. 5,631,973, the complete disclosure of which is incorporated herein by reference for all purposes.

As shown in FIG. 1, a servomechanism 16 is provided for transferring the mechanical motion of controllers 12 to manipulator assemblies 4. Servomechanism 16 may be separate from, or integral with manipulator assemblies 4. Servomechanism 16 will usually provide force and torque feedback from the surgical instruments 20 to the hand-operated controllers 12. In addition, servomechanism 16 will include a safety monitoring controller (not shown) that may freeze or at least inhibit all robot motion in response to recognized conditions (e.g., exertion of excessive force on the patient, "running away" of the manipulator assemblies 4, etc.). The servomechanism preferably has a servo bandwidth with a 3 dB cut off frequency of at least 10 hz so that the system can quickly and accurately respond to the rapid hand motions used by the surgeon. To operate effectively with this system, manipulator assemblies 4 have a relatively low inertia and the drive motors 170 (see FIG. 8) have relatively low ratio gear or pulley couplings. Any suitable conventional or specialized servomechanism may be used in the practice of the present invention, with those incorporating force and torque feedback being particularly preferred for telepresence operation of the system.

Figure 7:
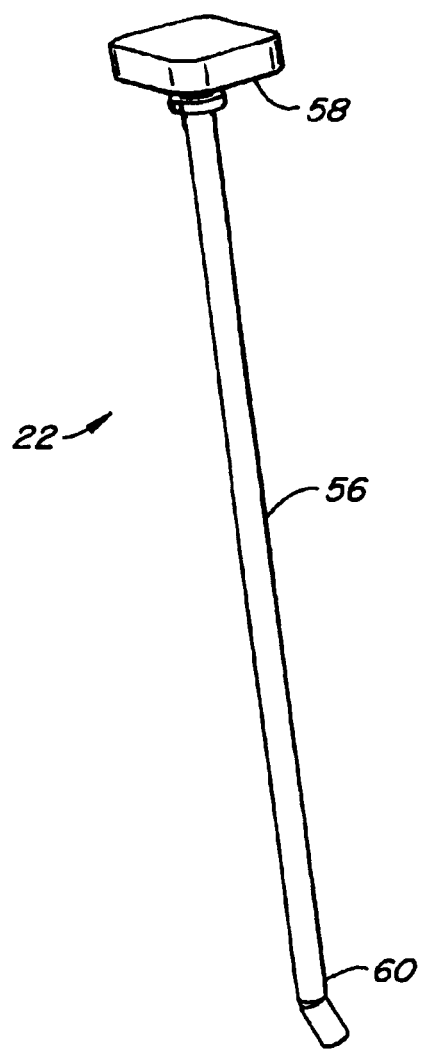
FIG. 7 is a perspective view of the wrist unit in accordance with an embodiment of the present invention.

Referring to FIG. 7, surgical instrument assemblies 20 each include a wrist unit 22 and a surgical tool 24 (FIGS. 3A and 3B) removably attached to wrist unit 22. As discussed in detail below, each wrist unit 22 generally includes an elongate shaft 56 having a proximal cap 58 and a distal wrist 60 pivotally coupled to surgical tool 24. Each wrist unit 22 is substantially the same, and will have different or the same surgical tools 24 attached thereto, depending on the requirements of the surgical procedure. Alternatively, wrist units 22 may have specialized wrists 60 designed for individual surgical tools 24 so that the wrist units 22 may be used with conventional tools 24. As shown in FIG. 1, the instrument assemblies 20 are usually assembled onto a table T or other suitable support adjacent the operating table O. According to a method of the present invention (described below), wrist units 22 and their associated surgical tools 24 can be quickly exchanged during the surgical procedure by coupling and decoupling wrist unit shafts 56 from manipulator assemblies 4.

Figure 2:
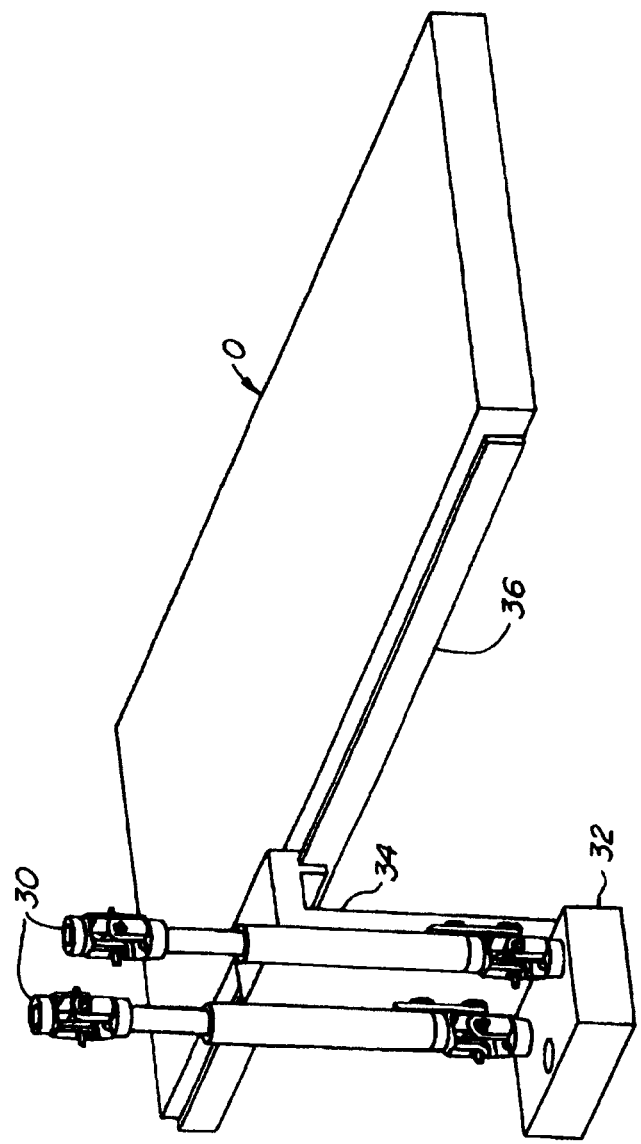
FIG. 2 is an enlarged view of the operating room of FIG. 1 illustrating a pair of mounting joints coupled to an operating table according to the present invention.

Referring to FIG. 2, each manipulator assembly 4 is preferably mounted to operating table O by a mounting joint 30. Mounting joints 30 provide a number of degrees of freedom (preferably at least 5) to assemblies 4, and they include a brake (not shown) so that assemblies 4 can be fixed at a suitable position and orientation relative to the patient. Joints 30 are mounted to a receptacle 32 for mounting joints 30 to operating table O, and for connecting each manipulator assembly 4 to servomechanism 16. In addition, receptacle 32 may connect joints 30 to other systems, such as an RF electrical power source, a suction-irrigation system, etc. Receptacle 32 includes a mounting arm 34 that is slidably disposed along an outer rail 36 of operating table O. Manipulator assemblies 4 may also be positioned over the operating table O with other mechanisms. For example, the system may incorporate a support system (coupled to the ceiling or a wall of the operating room) that moves and holds one or more manipulator assemblies 4 over the patient.

Referring now to FIGS. 3-8, manipulator assembly 4 will be described in further detail. Manipulator assembly 4 is a three-component apparatus that includes a non-sterile drive and control component, a sterilizable end effector or surgical tool (i.e., surgical instrument assembly 20), and an intermediate connector component. The intermediate connector includes mechanical elements for coupling the surgical tool 24 with the drive and control component, and for transferring motion from the drive component to the surgical tool 24. As shown in FIG. 3B, the drive and control component generally includes a drive assembly 40 and a multiple degree of freedom robotic arm 42 coupled to a mounting bracket 44, which is adapted for mounting onto mounting joints 30 (FIG. 2). Preferably, drive assembly 40 and robotic arm 42 are pivotally coupled to bracket 44 about an X-axis, which extends through a remote center of spherical rotation 45 (see FIG. 8, discussed in further detail below). Manipulator assembly 4 further includes a forearm assembly 46 fixed to a distal end 48 of arm 42, and a wrist unit adaptor 52 coupled to forearm assembly 46 for mounting wrist unit 22 and surgical tool 24 to manipulator assembly 4.

For endoscopic procedures, manipulator assembly 4 additionally includes a cannula adaptor 64 attached to a lower portion of forearm 46 for mounting a cannula 66 to manipulator assembly 4. Alternatively, cannula 66 may be an integral cannula (not shown) that is built into forearm assembly 46 (i.e., non-removable). Cannula 66 may include a force sensing element (not shown), such as a strain gauge or force-sensing resistor, mounted to an annular bearing within cannula 66. The force sensing bearing supports surgical tool 24 during surgery, allowing the tool to rotate and move axially through the central bore of the bearing. In addition, the bearing transmits lateral forces exerted by the surgical tool 24 to the force sensing element, which is connected to servomechanism 16 for transmitting these forces to controller(s) 12. In this manner, forces acting on surgical tools 24 can be detected without disturbances from forces acting on cannula 66, such as the tissue surrounding the surgical incision, or by gravity and inertial forces acting on manipulator assembly 4. This facilitates the use of manipulator assembly 4 in a robotic system because the surgeon will directly sense the forces acting against the surgical tool 24.

Figure 3A:
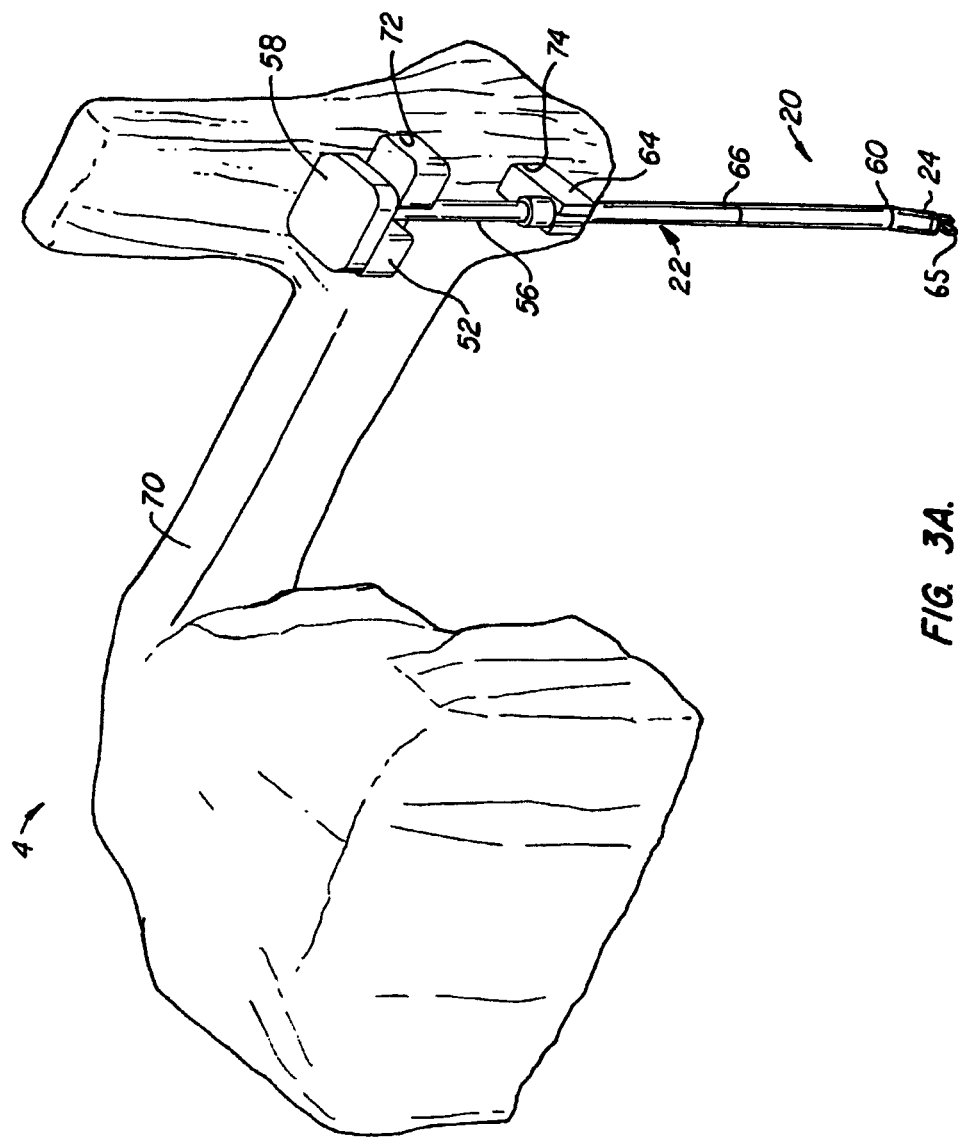
FIG. 3A is a perspective view of a robotic surgical manipulator that is partially covered by a sterile drape in accordance with an embodiment of the present invention.

As shown in FIG. 3A, manipulator assembly 4 further includes a sterile drape 70 sized to cover substantially the entire manipulator assembly 4. Drape 70 has a pair of holes 72, 74 sized and arranged so that wrist unit adaptor 52 and cannula adaptor 64 may extend through holes 72, 74 to mount wrist unit 22 and cannula 66 to manipulator assembly 4. Sterile drape 70 comprises a material configured to effectively shield manipulator assembly 4 from the surgical site so that most of the components of assembly 4 (i.e., arm 42, drive assembly 40 and forearm assembly 46) do not have to be sterilized prior to, or following the surgical procedure.

As shown in FIG. 3A, wrist unit adaptor 52 and cannula adaptor 64 extend through holes 72, 74 of drape 70 so that forearm assembly 46 and the remainder of manipulator assembly 4 remain shielded from the patient during the procedure. In one embodiment, wrist unit adaptor 52 and cannula adaptor 64 are manufactured as reusable components that will be sterilized because these components extend into the sterile field of the surgical site. Wrist unit and cannula adapters 52, 64 may be sterilized by normal methods, i.e., steam, heat and pressure, chemicals and the like. Referring again to FIG. 3B, wrist unit adaptor 52 includes an opening 80 for receiving shaft 56 of wrist unit 22. As discussed in detail below, shaft 56 can be laterally urged through opening 80 and snap-fit into adaptor 52 such that the non-exposed portion of wrist unit adaptor 52 remains sterile (i.e., remains on the sterile side of drape 70 opposite the sterile field). Wrist unit adaptor 52 may also include a latch (not shown) for securing wrist unit 22 therein. Similarly, cannula adaptor 64 includes an opening 82 for snap fitting cannula 66 thereto such that the non-exposed portion of adaptor 64 remains sterile during the surgical procedure.

Figure 4:
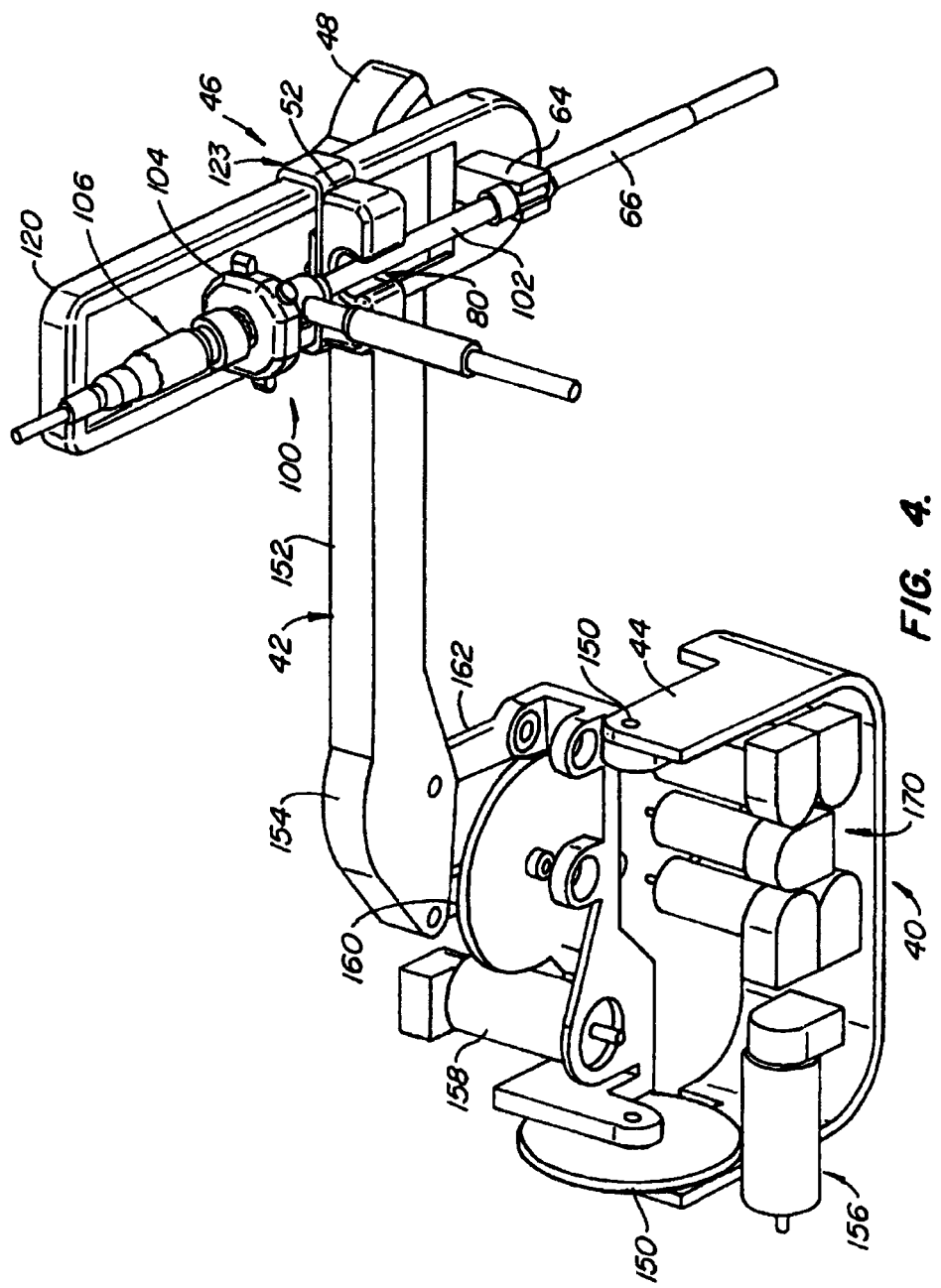
FIG. 4 illustrates the robotic surgical manipulator of FIGS. 3A-3B incorporating a camera and endoscope for viewing the surgical site.

As shown in FIG. 4, wrist unit adaptor 52 may also be configured to receive a viewing scope 100 for viewing the surgical site. For endoscopic procedures, viewing scope 100 can be a conventional endoscope, which typically includes a rigid, elongated tube 102 containing a lens system (not shown) and a camera mount 104 at the proximal end of the tube 102. A small video camera 106 is preferably attached to the camera mount 104 and connected to video monitor 10 to provide a video image of the procedure. Preferably, the scope 100 has a distal end (not shown) configured to allow lateral or angled viewing relative to tube 102. The viewing scope may also have a guidable tip that can be deflected or rotated by manipulating an actuator on a proximal end of tube 102. This type of scope is commercially available from Baxter Healthcare Corp. of Deerfield, Ill., or Origin Medsystems, Inc. of Menlo Park, Calif.

As shown in FIG. 4, viewing scope 100 further includes a scope adaptor 110 for coupling viewing scope 100 to wrist unit adaptor 52. Scope adaptor 110 is sterilizable, ETO and autoclavable, and it includes a plurality of motion feedthroughs (not shown) for transferring motion from drive assembly 40 to scope 100. In the preferred configuration, the motion includes pitch and yaw motion, rotation about the Z-axis, and movement along the Z-axis.

Figure 5:
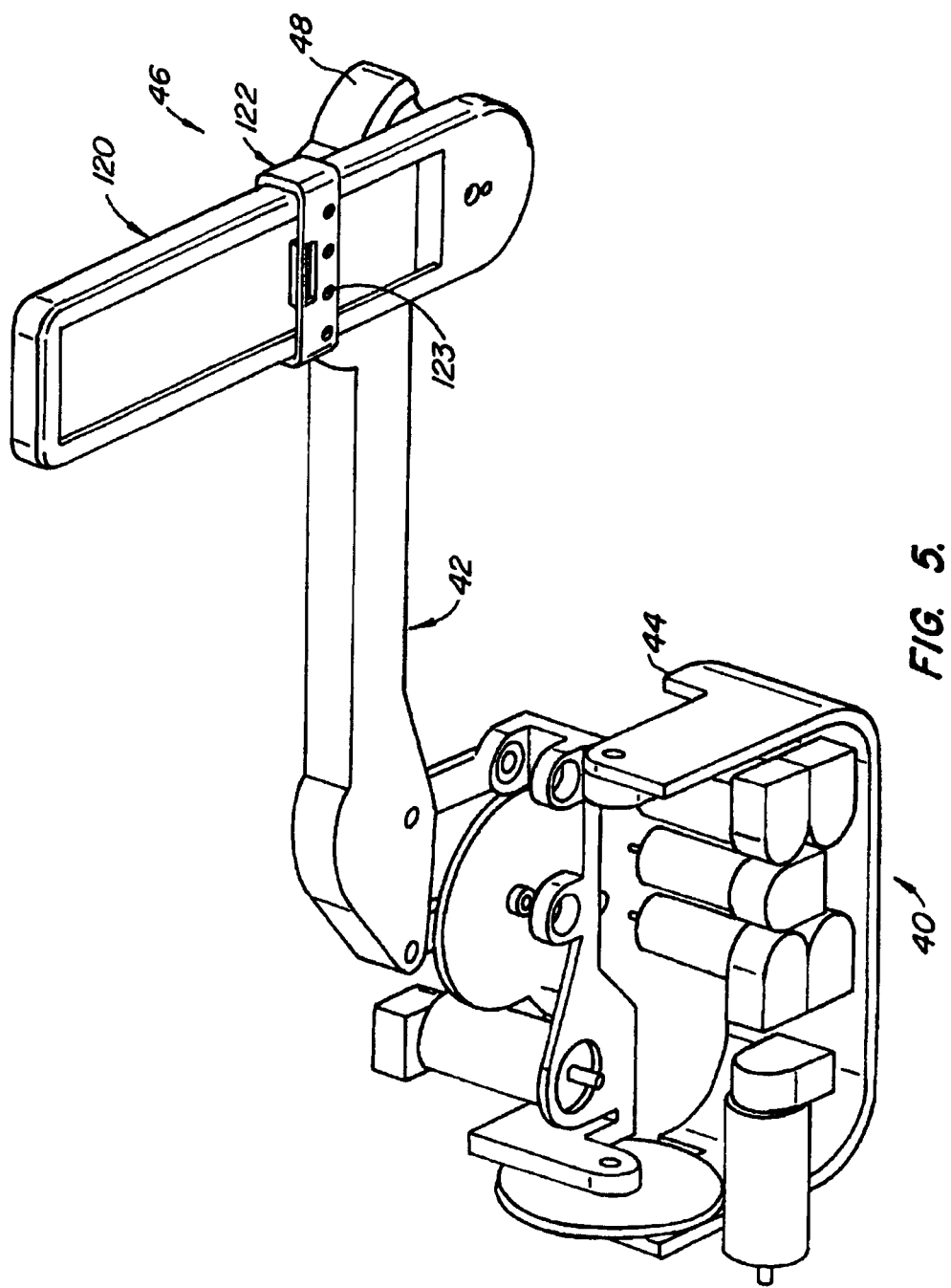
FIG. 5 is a partial view of the robotic manipulator of FIGS. 3A-3B, illustrating mechanical and electrical couplings between the arm and the wrist unit.
Figure 6:
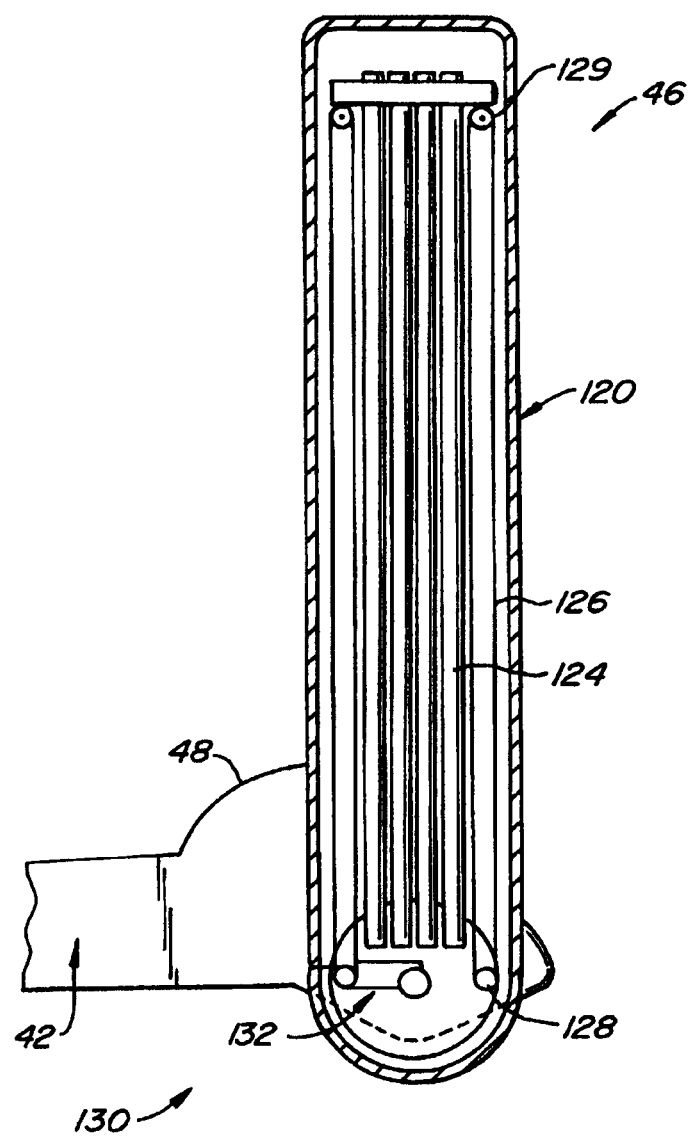
FIG. 6 is a partially cut-away sectional view of a forearm and a carriage of the manipulator of FIGS. 3A and 3B.

Referring now to FIGS. 5 and 6, forearm assembly 46 will be described in further detail. As shown in FIG. 5, forearm assembly 46 includes a housing 120 fixed to arm 42 and a movable carriage 122 slidably coupled to housing 120. Carriage 122 slidably mounts wrist unit adaptor 52 to housing 120 for moving wrist unit adaptor 52 and wrist unit 20 in the Z-direction. In addition, carriage 122 defines a number of openings 123 for transferring motion and electrical signals from forearm assembly 46 to wrist unit adaptor 52. As shown in FIG. 6, a plurality of rotatable shafts 124 are mounted within housing 120 for transferring motion from arm 42 through openings 123 to wrist unit adaptor 52 and wrist unit 22. Rotating shafts 124 preferably provide at least four degrees of freedom to wrist unit 22, including yaw and pitch motion of surgical tool 24 about wrist 60 of wrist unit 22, rotation of wrist unit 22 about the Z-axis and actuation of tool 24. The system may also be configured to provide more or less degrees of freedom, if desired. Actuation of tool 24 may include a variety of motions, such as opening and closing jaws, graspers or scissors, applying clips or staples and the like. Motion of wrist unit 22 and tool 24 in the Z direction is provided by a pair of carriage cable drives 126 extending between rotatable pulleys 128, 129 on either end of forearm housing 120. Cable drives 126 function to move carriage 122 and wrist unit 22 in the Z direction relative to forearm housing 120.

As shown in FIG. 6, distal end 48 of arm 42 includes a coupling assembly 130 having a plurality of motion feed-throughs 132 for transferring motion from arm 42 to forearm assembly 46. In addition, coupling assembly 130 includes a number of electrical connectors (not shown) for transferring electrical signals from arm 42 to wrist unit 22. Similarly, wrist unit adaptor 52 includes a plurality of motion feed-throughs (not shown) and electrical connections (not shown) for transferring motion, and for sending and receiving electrical signals to and from wrist unit 22 (e.g., for sending and receiving force and torque feedback signals from the surgical site to controllers 12). The components on either side of coupling assembly 130 and wrist unit adaptor 52 have a finite range of motion. Usually, this range of motion will be at least 1 revolution and preferably greater than 1 revolution. These ranges of motion are aligned with each other when the forearm assembly 46 is mechanically coupled to the coupling assembly 130 and when wrist unit adaptor 52 is mechanically coupled to the forearm 46.

Referring to FIG. 7, wrist unit 22 will now be described in further detail. As shown, wrist unit 22 includes a hollow shaft 56 having a cap 58 attached to its proximal end and a wrist 60 attached to its distal end. Wrist 60 includes a coupling (not shown) for removably coupling a variety of surgical tools 24 to shaft 56. Shaft 56 is rotatably coupled to cap 58 for providing rotation of shaft 56 and tool 24 about the longitudinal axis of shaft 56 (i.e., the Z axis). Cap 58 houses a mechanism (not shown) for transferring motion from wrist unit adaptor 52 to drive cables (not shown) within shaft 56. The drive cables are suitably coupled to drive pulleys within shaft 56 to pivot tool 24 about wrist 60, and to actuate end effectors 140 on tool 24. Wrist 60 may also be operated by other mechanisms, such as differential gears, push-rods, or the like.

Tool 24 is removably coupled to wrist 60 of wrist unit 22. Tool 24 will preferably include an end effector 65 (FIGS. 3A and 3B) having a tactile sensor array (not shown) for providing tactile feedback to the surgeon. Tool 24 may include a variety of articulated tools, such as jaws, scissors, graspers, needle holders, micro dissectors, staple appliers, tackers, suction irrigation tools, clip appliers, that have end effectors driven by wire links, eccentric cams, push-rods or other mechanisms. In addition, tool 24 may comprise a non-articulated instrument, such as cutting blades, probes, irrigators, catheters or suction orifices. Alternatively, tool 24 may comprise an electrosurgical probe for ablating, resecting, cutting or coagulating tissue. In the latter embodiment, wrist unit 22 will include a conductive element, such as a proximal banana plug coupled to a lead wire or rod extending through shaft 56 to tool 24.

Figure 8:
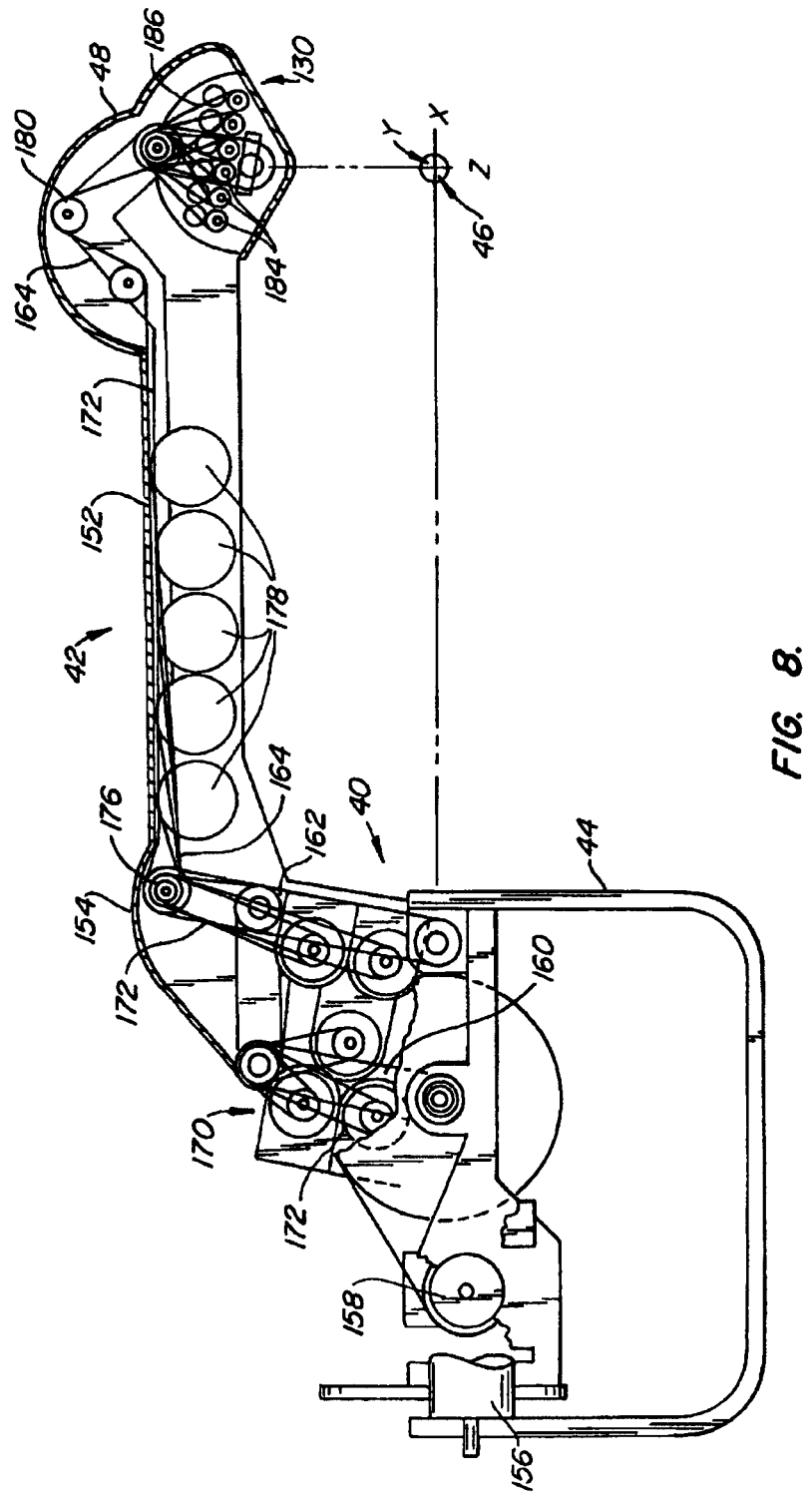
FIG. 8 is a side cross-sectional view of a portion of the robotic manipulator, illustrating the arm and the drive assembly.

Referring to FIGS. 4 and 8, a specific configuration of the drive and control component of the present invention (i.e., the robotic arm 42 and drive assembly 40) will be described in further detail. As discussed above, arm 42 and drive assembly 40 are rotatably coupled about a pair of pins 150 extending from mounting bracket 44. Arm 42 preferably comprises an elongate, substantially rigid body 152 with a distal end 48 coupled to forearm assembly 48 and a proximal end 154 pivotally coupled to drive assembly 40 and bracket 44 for rotation about pitch and yaw or the X and Y axes (note that the Y axis is perpendicular to the page and extends through point 45, see FIG. 8). Arm 40 may have other configurations, such as an elbow arm (similar to the human arm), prismatic arm (straight extendable) or the like. A stationary yaw motor 156 is mounted to mounting bracket 44 for rotating arm 42 and drive assembly 40 about the X-axis. Drive assembly 40 also includes a pitch motor 158 coupled to arm 42 for rotating arm about the Y axis. A pair of substantially rigid linkage elements 160, 124 extend from bracket 44 to robotic arm 42 to pivotally couple arm 42 to bracket 44 about Y-axis. One of the linkage elements 160 is pivotally coupled to arm 42, and the other linkage element 124 is pivotally coupled to a third linkage element 164 extending parallel to arm 42. Preferably, robotic arm 42 is a channel shaped rigid element that at least partially houses the third linkage element 164. The linkage elements 160, 124 and 164 and arm 42 form a parallelogram linkage in which the members are connected together in a parallelogram for relative movement only in the plane formed by the members.

The Z-axis of wrist unit 22 held at the distal end 48 of arm 42 intersects the x axis of the parallelogram linkage described above. Wrist unit 22 has a remote center of spherical rotation about the position indicated by the numeral 45 in FIG. 8. Thus, the distal end of wrist unit 22 can be rotated about its own axis or the X and Y axes while the remote center of rotation 45 remains at the same location. A more complete description of a remote center positioning device can be found in U.S. patent application Ser. No. 08/504,301, filed Jul. 20, 1995, now U.S. Pat. No. 5,931,832, the complete disclosure of which is incorporated herein by reference for all purposes. It should be noted that arm 42 and drive assembly 40 may be used with a broad range of positioning devices other than that described above and shown in FIG. 8, such as a stereotaxic positioner, a fixed gimbal, or the like.

Referring again to FIG. 8, drive assembly 40 further includes a plurality of drive motors 170 coupled to arm 42 for rotation therewith. Pitch and yaw motors 156, 158 control the motion of arm 42 (and drive motors 170) about the X and Y axes and drive motors 170 control the motion of wrist unit 22 and surgical tool 24. Preferably, at least five drive motors 170 are coupled to arm 42 for providing at least five degrees of freedom to wrist unit 22. Drive motors 170 will preferably include encoders (not shown) for responding to servomechanism 16 and force sensors (not shown) for transmitting force and torque feedback to the surgeon S. As discussed above, the five degrees of freedom preferably include movement of carriage 122 and wrist unit 22 in the Z-direction, rotation of wrist unit 22 about the Z-axis, pitch and yaw rotation of surgical tool 24 around wrist 60 and actuation of tool 24.

As shown, cables 172 extend from each motor 170 around a motor drive pulley 174, an idler pulley 176 within arm 42 and along a relatively large pot capstan 178 to minimize the effect of friction torque on cables 172. The cables 172 each extend around another idler pulley 180 at distal end 48 of arm 42, around a coupling drive pulley 182 and back to the motor 170. The cables 172 will preferably be tensioned at the motor drive pulley 174 and anchored there as well as at the coupling drive pulley 182. As shown in FIG. 8, coupling drive pulley 182 is connected to a plurality of smaller pulleys 184 within coupling assembly 130 via a plurality of cables 186 for transferring motion from the motors 170 to wrist unit adaptor 52.

A method for performing a surgical procedure on a patient according to the present invention will now be described with reference to FIGS. 1-9. As shown in FIG. 2, mounting joints 30 are attached to receptacle 32, which is attached to the operating table O by sliding mounting arm 34 along rail 36. Each manipulator assembly 4 is then attached to its respective mounting joint 30 and articulated into the proper position and orientation relative to the patient P. Receptacles 32 are then coupled to, servomechanism 16 and other systems that may be required during the surgical procedure, such as an RF power supply, a suction/irrigation system, etc. Sterile drapes 70 are placed over the manipulator assemblies 4 before, during, or after the patient has been anesthetized (FIG. 3A). To prepare for the surgical procedure, manipulator assemblies 4 may or may not be chemically cleaned prior to covering them with drapes 70. Wrist unit adapters 52, cannula adapters 64, and scope adapters 110 are snapped onto forearm assemblies 46 of manipulator assemblies 4 (see FIGS. 3B and 5). The number and relative positions of scope adapters 110 and wrist unit adapters 52 will, of course, depend on the individual surgical procedure (e.g., cannula adapters 64 may not be required for open surgical procedures).

During the surgical procedure, surgical instrument assemblies 20 are coupled to their respective manipulator assemblies 4 by laterally urging each respective wrist unit shaft 56 through opening 80 of wrist unit adaptor 52. Each wrist unit 22 will have suitable identification means (not shown) to quickly and easily indicate what type of tool 24 is connected to the wrist unit 22. When the surgeon wishes to change surgical tools 24, he or she manipulates controller(s) 12 so that carriage 122 moves to a top or proximal position of travel along forearm assembly 46 (see FIG. 3B). In this position, surgical tool 24 is within cannula 66 or during open procedures, removed from the surgical site. The assistant(s) A then pulls upward on wrist cap 58 to release the latch (not shown), thereby allowing wrist unit 22 to slide further upwards and out of cannula 66. The assistant(s) A may then pull wrist unit 22 laterally to decouple it from wrist unit adaptor 52. When wrist unit 22 is no longer coupled to adaptor 52, the control mechanism understands that the system is in "tool change mode", and drives carriage 122 to the proximal position if it has not already been moved there by the surgeon.

Figure 3B:
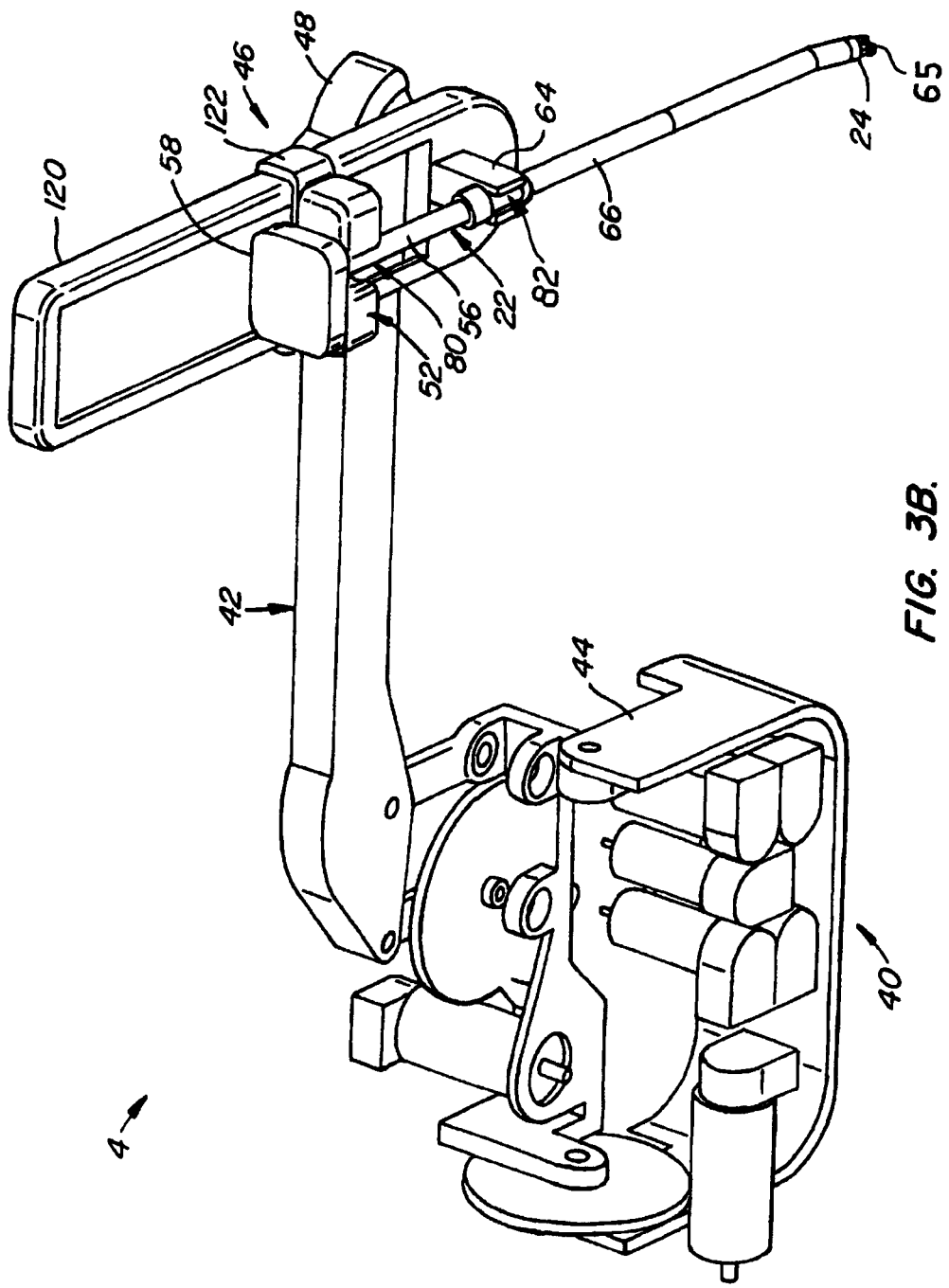
FIG. 3B is a perspective view of the robotic surgical manipulator of FIG. 3A without the sterile drape to illustrate a multiple degree of freedom arm coupling a driving assembly with a wrist unit and a surgical tool.

To couple another surgical instrument assembly 20 to manipulator assembly 4, the assistant(s) A grabs another assembly 20 from table T, laterally urges wrist unit shaft 56 into opening 80 of wrist unit adaptor 52, and then moves wrist unit 22 downward so that surgical tool 24 resides within cannula 66 (see FIGS. 1 and 3B). This downward movement of wrist unit 22 automatically mates the electrical couplings and motion feed-throughs (not shown) within wrist cap 58 and wrist unit adaptor 52. The system may include a control mechanism configured to lock carriage 122 travel at the top or proximal position, e.g., by actuating a brake (not shown), until the couplings are mated and wrist unit 22 is no longer being moved downward. At this point, the surgeon S may continue the surgical procedure.

The system and method of the present invention preferably includes a mechanism for counting the number of times wrist unit 22 is decoupled and coupled from wrist unit adaptor 52. In this manner, the manufacturer may limit the number of times wrist unit 22 can be used. In a specific configuration, an integrated circuit chip (not shown) is housed within wrist cap 58. The circuit chip counts the number of times wrist unit 22 is coupled to wrist unit adaptor 52, e.g., 20 times, and a warning shows up on the surgeon's console C. The control system then downgrades the performance of the system by reducing the load it can deliver or increasing apparent backlash.

Figure 9A:
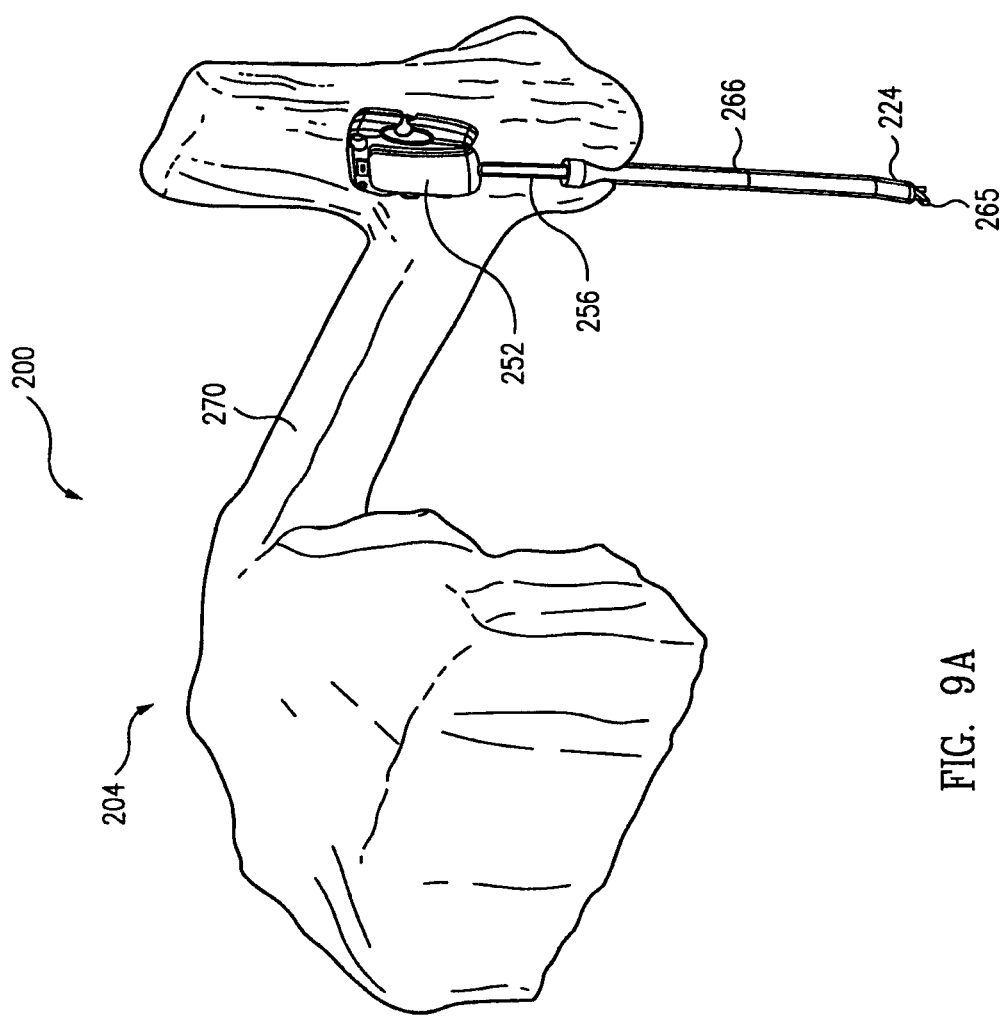
FIG. 9A is a perspective view of a robotic surgical manipulator that is partially covered by a sterile drape in accordance with another embodiment of the present invention.
Figure 9B:
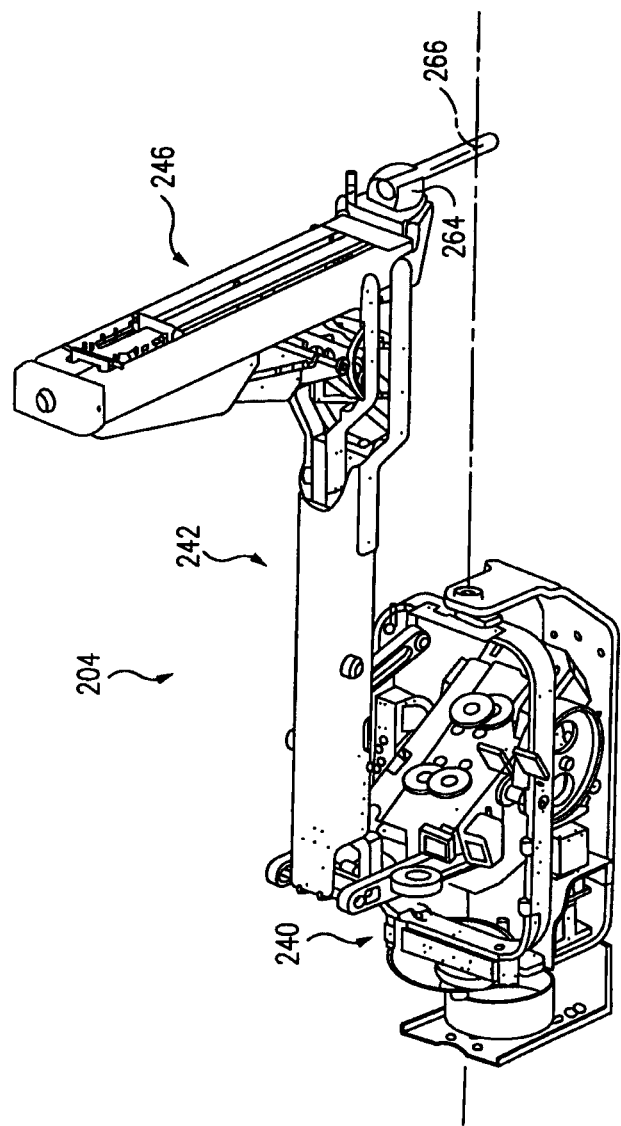
FIGS. 9B-9C are views of the robotic surgical manipulator of FIG. 9A without the sterile drape to illustrate a multiple degree of freedom arm coupling a driving assembly with a surgical accessory clamp, a wrist unit, and a surgical tool.
Figure 9C:
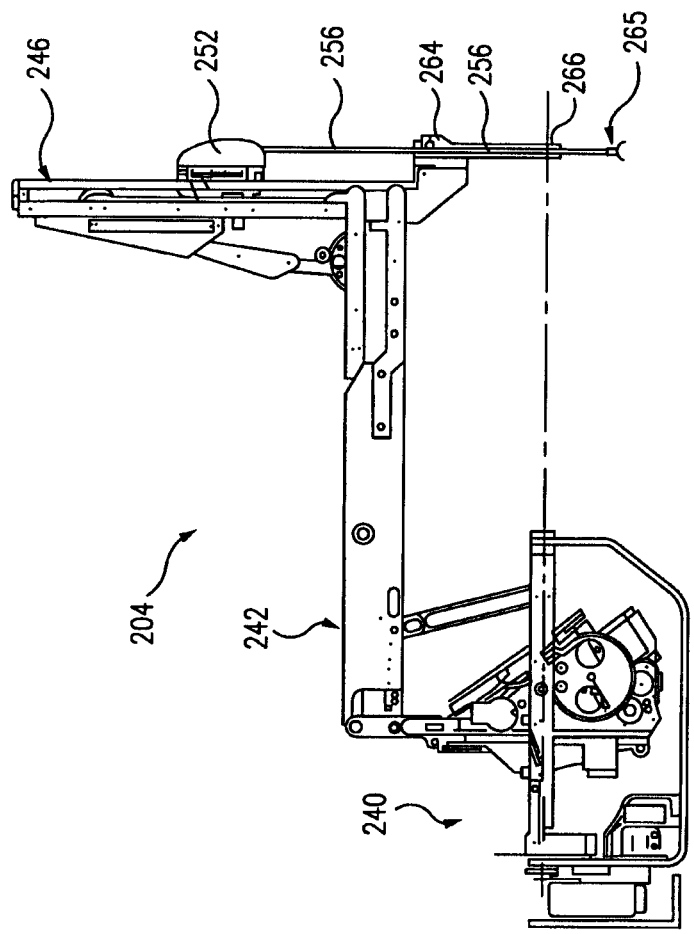

Referring now to FIG. 9A, a robotic surgical system 200 including a robotic surgical manipulator 204 that is partially covered by a sterile drape 270 is shown in accordance with another embodiment of the present invention. FIGS. 9B and 9C are views of the robotic surgical manipulator of FIG. 9A without the sterile drape to illustrate a multiple degree of freedom arm coupling a driving assembly with a surgical accessory clamp, a wrist unit, and a surgical tool. System 200 is similar to the system shown and described above with respect to FIGS. 1-8 but a surgical accessory clamp 264 does not extend through sterile drape 270 and interfaces with a surgical accessory 266 (e.g., a cannula) with a portion of drape 270 effectively shielding accessory clamp 264 from the sterile field of the surgery during the procedure. Advantageously, accessory clamp 264 is not required to be sterilized or replaced prior to a surgical procedure, thus allowing for cost savings, and since there is one less opening through the sterile drape, system 200 is better shielded from the sterile field allowing for greater insulation of the system equipment.

The same or similar manipulator assembly 4 including drive assembly 40, arm 42, forearm assembly 46, wrist unit adaptors 52, wrist units 22, and tools 24 (with the same or similar functionality) described above may be used within system 200 and with accessory clamp 264, and repeated description of the same or similar part is omitted. However, a different drive assembly 240, arm 242, forearm assembly 246, and interface 252 to actuate tool 224 with shaft 256 and end effectors 265 is illustrated in FIGS. 9A-9C. Embodiments of drive assembly 240, arm 242, forearm assembly 246, interface 252, and other applicable parts or tools are described for example in U.S. Pat. Nos. 6,331,181, 6,491, 701, and 6,770,081, the full disclosures of which (including disclosures incorporated by reference therein) are incorporated herein by reference for all purposes. Embodiments of clamps 264, accessories 266, and portions of drape 270 will now be described in more detail.

Figure 10:
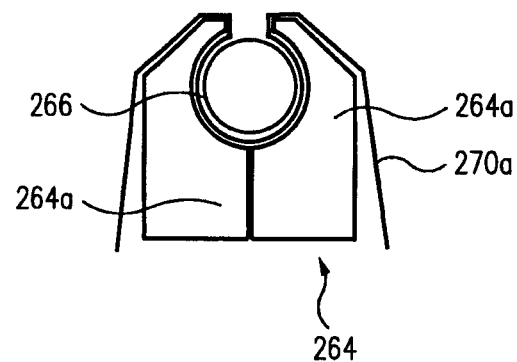
FIG. 10 is a cross-section view of the surgical accessory clamp, surgical accessory, and sterile drape portion therebetween, in accordance with an embodiment of the present invention.

FIG. 10 is a cross-section view of surgical accessory clamp 264, surgical accessory 266, and a sterile drape portion 270a of sterile drape 270 therebetween, in accordance with an embodiment of the present invention. Surgical accessory clamp 264 includes two clamp jaws 264a that are actuated to "capture" accessory 266 therebetween. One or both jaws 264a may be active or actuable. In one embodiment, a lever portion may actuate jaws 264a by a sliding motion or a pivot motion.

Figure 11B:
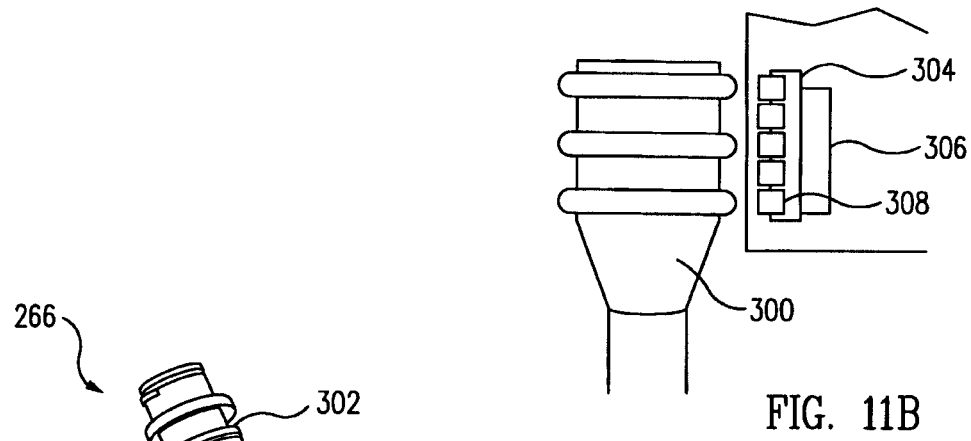
FIGS. 11A-11C illustrate a cannula as a surgical accessory and a cross-section of a sensing mechanism for the accessory in accordance with an embodiment of the present invention.
Figure 11A:
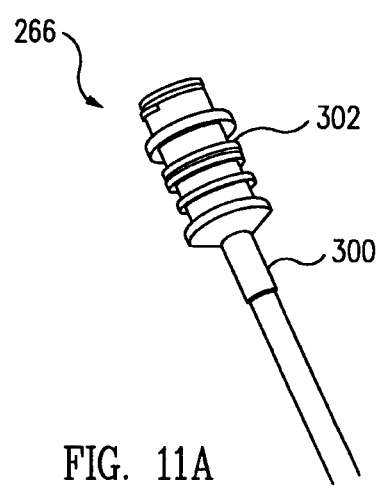
Figure 11C:
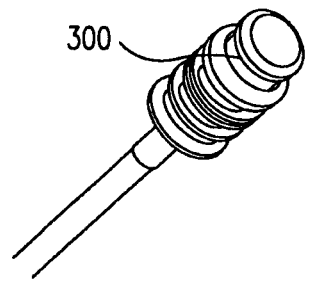

FIGS. 11A-11C illustrate an example of surgical accessory 266, such as a cannula 300, in accordance with an embodiment of the present invention. Optionally, cannula 300 includes rings 302 for automatic identification of the cannula type to surgical system 200, providing for example information verifying that the accessory is compatible with the particular robotic system, system reconfiguration parameters if needed, and accessory-specific information such as tool-life data, cannula length, general presence, or the like. For reading information from rings 302, a printed circuit board (PCB) 304, a magnet 306, and sensors 308 may be a part of accessory clamp 264 or forearm assembly 246 (FIGS. 9B and 9C). It is noted that the present invention is not limited to a cannula accessory but various accessories 266 are within the scope of the invention, including but not limited to reusable or disposable accessories that can be attached or removed from the robot arm during any time of a surgical procedure, such as endoscope/camera assemblies and surgical instruments (e.g., a retractor or a stabilizer).

Figure 12A:
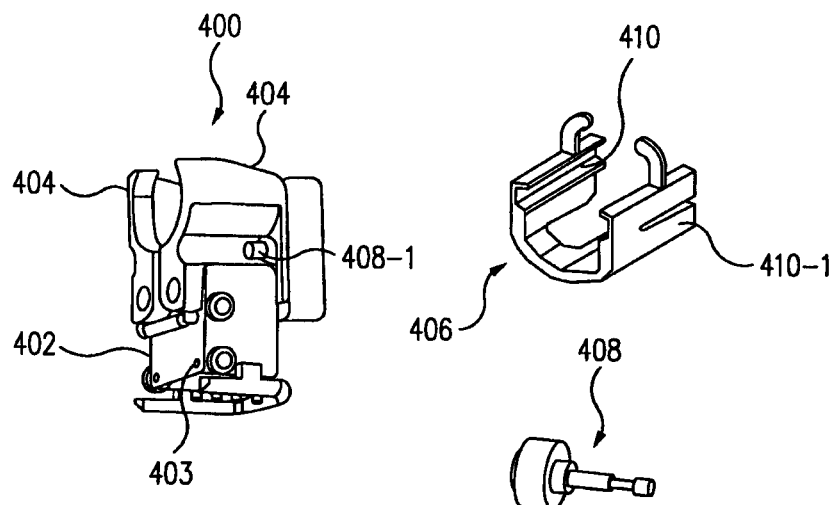
FIGS. 12A-12C illustrate different views of a surgical accessory clamp in accordance with an embodiment of the present invention.
Figure 12B:
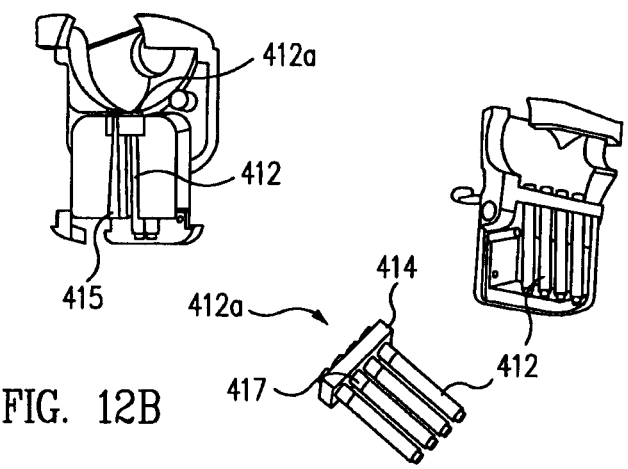
Figure 12C:
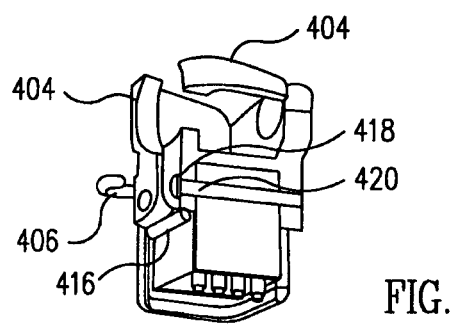
Figure 13A:
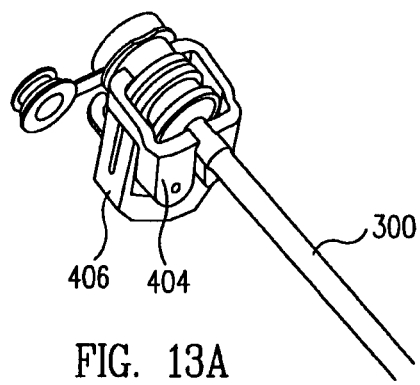
FIGS. 13A-13B illustrate perspective views of a surgical accessory retained in the surgical accessory clamp of FIGS. 12A-12C in accordance with an embodiment of the present invention.
Figure 13B:
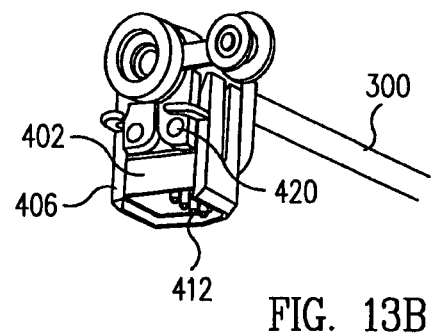

FIGS. 12A-12C illustrate different views of a surgical accessory clamp 400 in accordance with an embodiment of the present invention. Accessory clamp 400 includes a base 402 for coupling to a distal end of a robotic manipulator arm (e.g., forearm assembly 246), two clamp jaws 404, and a lever portion 406 for actuating the two clamp jaws 404 into an open position or a closed position. Different parts of accessory clamp 400 are highlighted in FIGS. 12A and 12B and a cut perspective of the assembly is shown in FIG. 12C. FIGS. 13A and 13B show full assembly illustrations with a clamped accessory.

As shown in FIG. 12A, in this particular embodiment of a clamp, a cam follower 408 runs along grooves 410 in lever portion 406 as lever portion 406 moves up and down relative to base 402 to guide the lever for smooth operation. As the lever moves up, a second cam follower 408-1 interacts with a ramped section of the lever 410-1 that activates the clamp jaws 404 between the open position and the closed position (see FIGS. 14A-14C). The ramped section acts as a cam and a spring that partially determines the load applied to the accessory and the load required to close the lever. In addition the cam has a high-point that creates an over-center feature to keep the clamp closed and give positive feedback to the user that the clamp is engaged. Set screws 403 allow for a redundant retaining method for the guide cam followers. Referring now to FIG. 12B, sensors 412 pre-assembled into a block 414 are positioned by locating pins 417 within base 402 such that sensor ends 412a have fixed positions ideal for sensing identification information from a clamped accessory, such as cannula 300 (FIGS. 11A-11C). Screws 415 allow base 402 to be coupled to the manipulator arm. It should be understood that various other means could be used to couple base 402 to the manipulator arm, such as by adhesive or welding material. FIG. 12C illustrates pivot pins 420 (e.g., 8-32 threads 418) that act as the pivot axes for clamp jaws 404 as they move between the open and closed positions. Clamp jaws 404 are biased into the open position in this embodiment via a spring 416 between the clamp jaws which keep the clamp jaws in the open position unless actuated into the closed position by lever portion 406. It should be understood that the clamp could also be designed such that the clamp jaws are naturally in the closed position unless actuated into the open position.

FIGS. 13A and 13B illustrate perspective views of assembled surgical accessory clamp 400 of FIGS. 12A-12C in accordance with an embodiment of the present invention. Cannula 300 is locked-in between clamp jaws 404 which are in the closed position.

Figure 14A:
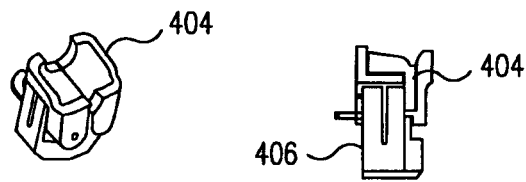
FIGS. 14A-14C illustrate perspective and side views for positioning and clamping a surgical accessory in the surgical accessory clamp of FIGS. 12A-12C in accordance with an embodiment of the present invention.
Figure 14B:
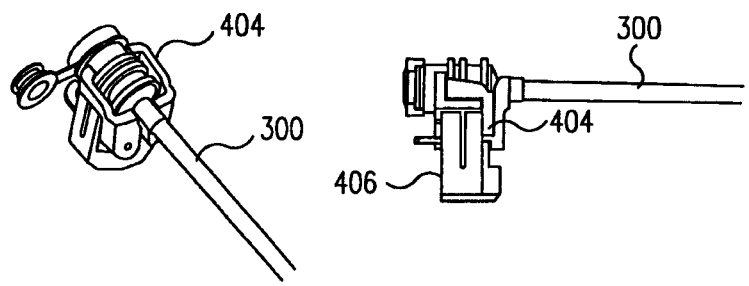
Figure 14C:
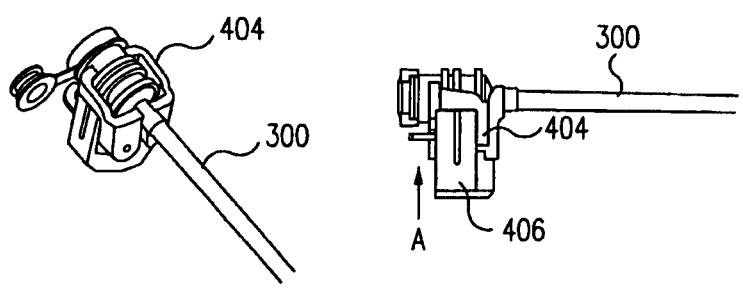

FIGS. 14A-14C illustrate perspective and side views for the positioning and clamping of cannula 300 in surgical accessory clamp 400 of FIGS. 12A-12C in accordance with an embodiment of the present invention. FIG. 14A shows accessory clamp 400 in a first (open) position, clamp jaws 404 being biased open by spring 416 therebetween. FIG. 14B shows accessory 400 positioned between clamp jaws 404. FIG. 14C shows accessory clamp 400 in a second (closed) position as lever portion 406 is pushed upward relative to base portion 402 toward clamp jaws 404 along the direction of arrow A, thereby actuating clamp jaws 404 into the closed position. Accordingly, clamp jaws 404 are actuated by sliding lever portion 406 toward clamp jaws 404. In other embodiments, a pivoting lever portion will be shown and described below with respect to FIGS. 19-23.

Figure 15:
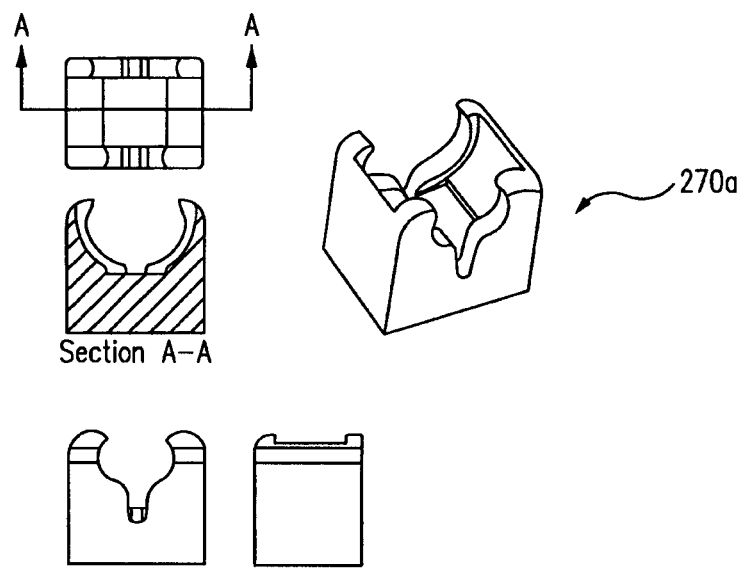
FIGS. 15 and 16 illustrate two sterile drape portions that may fit over clamp jaws of the accessory clamp.
Figure 16:
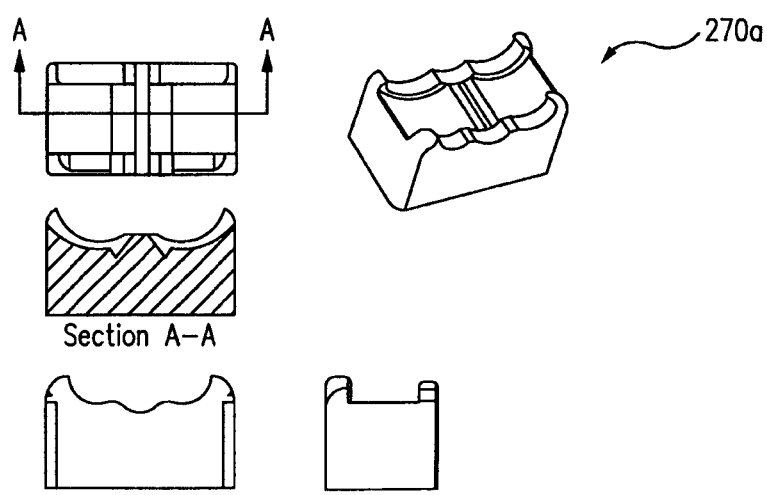

FIGS. 15 and 16 illustrate different views of two examples of sterile drape portions 270a that may fit over clamp jaws 404 of accessory clamp 400 illustrated in FIGS. 12A-12C. Sterile drape portion 270a is formed to fit to the shape of clamp jaws 404, and flexes along with the active components of the clamp jaws. Thus, drape portion 270a has a surface shaped (in this case cylindrical) to receive and clamp the accessory in the closed position.

Sterile drape portion 270a is preferably comprised of material of sufficient rigidity and strength to allow proper placement onto the non-sterile accessory clamp and to resist tearing even under application of cyclical loads in various directions, but is preferably comprised of material of sufficient flexibility to allow movement with the active sections of the clamp jaws. Sterile drape portion 270a can be formed as part of a single drape or a separate piece that can be attached to the main sterile drape 270 via adhesive, heat, RF welding, or other means.

Figure 17A:
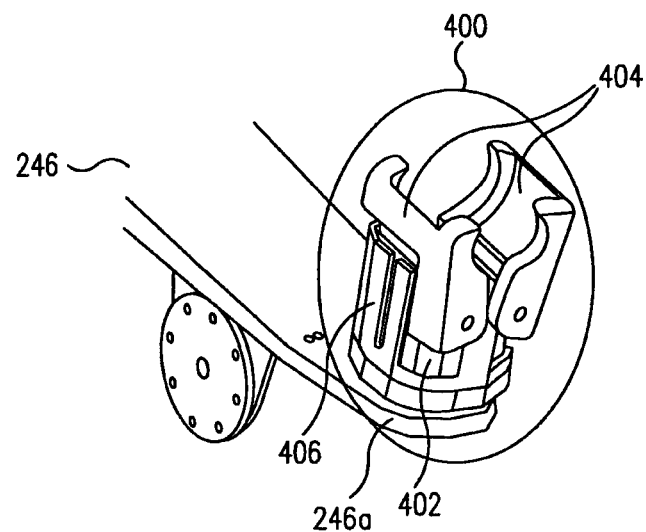
FIGS. 17A-17E illustrate perspective views for positioning a sterile drape portion over the clamp jaws of the accessory clamp and then clamping the accessory between the clamp jaws.
Figure 17B:
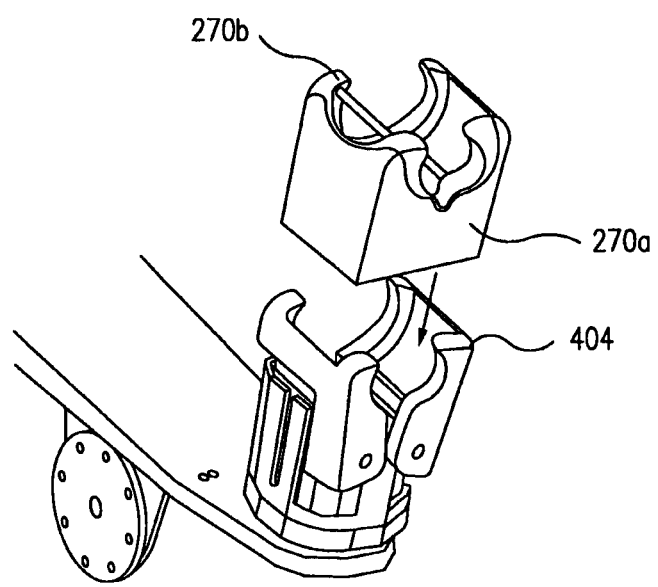
Figure 17C:
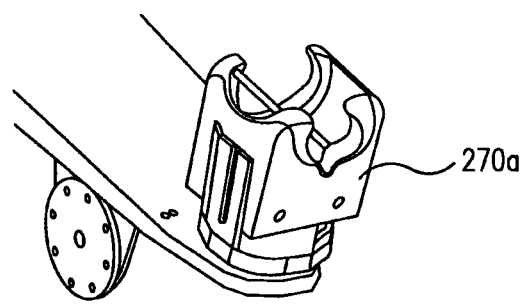

FIGS. 17A-17E illustrate perspective views for positioning sterile drape portion 270a over clamp jaws 404 of the accessory clamp and then clamping cannula 300 between the clamp jaws with sterile drape portion 270a between the clamp jaws and the accessory. FIG. 17A shows accessory clamp 400 mounted at the distal end of a robot arm, such as a cannula mount section 246a of the end of forearm assembly 246. FIG. 17B shows sterile drape portion 270a being positioned over clamp jaws 404, and FIG. 17C shows drape portion 270a fully positioned over accessory clamp 400. In one embodiment, sterile drape portion 270a may include a reinforcement 270b that is coupled to the top surface of drape portion 270a, for example being bonded or heat staked together. Reinforcement 270b may be comprised of various durable materials, and in one example is comprised of high-density polyethylene (HDPE) or polyurethane.

Figure 17D:
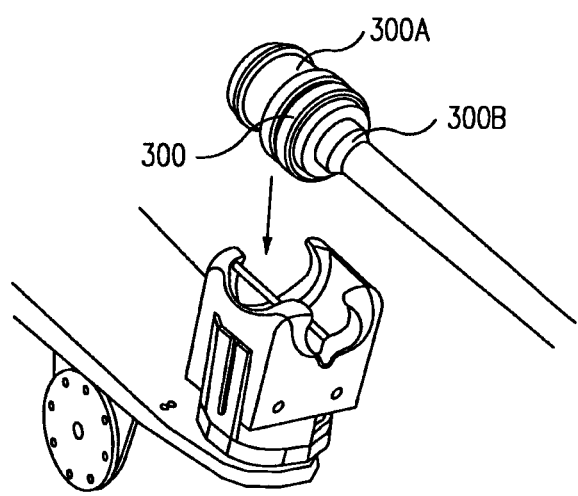

FIG. 17D shows cannula 300 being positioned over clamp 400. Advantageously, cannula 300 may be positioned in any axial orientation desired prior to being clamped between the clamp jaws in the closed position. Features on the accessory may physically limit the user from attaching the cannula incorrectly. In one example, two specific diameter clamping sections 300A and 300B are defined on the accessory for clamping. The diameters are different sizes to insure that the accessory can not be clamped incorrectly. The larger diameter in the jaws 404 is large enough that if the smaller diameter clamping section 300B is placed in the area inside the jaws the accessory will not be held if the lever is closed. The smaller diameter in the jaws 404 and the limited open angle of the jaws make it such that the larger diameter clamping section 300A would not physically fit in that area.

Figure 17E:
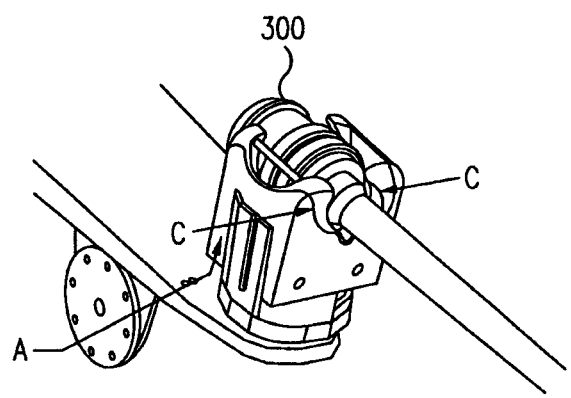

FIG. 17E shows cannula 300 fully clamped between clamp jaws 404 of clamp 400, with clamp jaws 404 in the closed position as they move inward in the direction of arrows C as lever portion 406 is moved upward in the direction of arrow A. Cannula 300 is now rigidly and precisely attached to the robotic arm with the sterile drape portion between the cannula and the clamp.

Advantageously, a surgical accessory may be attached and removed from a manipulator arm during a surgical procedure without requiring the use of an intermediate sterile accessory clamp, thus removing the need for a detachable accessory mount or adaptor that needs cleaning and sterilization and allowing for greater efficiency and cost-effectiveness. The present invention further allows for easy removal and attachment of instruments, tools, or accessories to the robotic surgical system without breach of sterility, for example allowing accessory exchange with but a single hand in some instances.

Figure 18A:
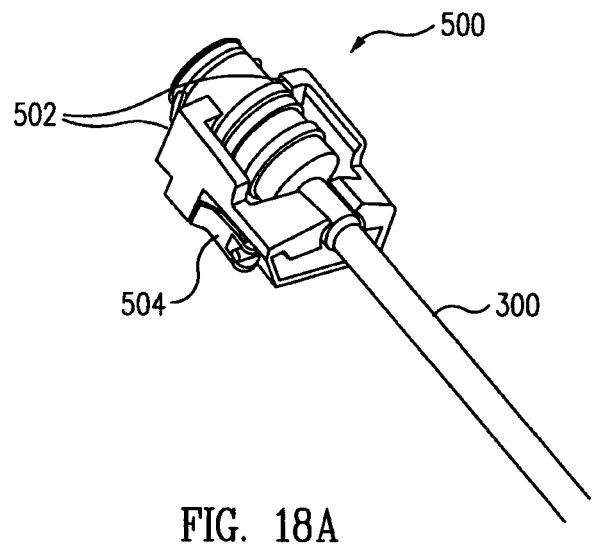
FIGS. 18A-18C illustrate views of a slide accessory clamp in accordance with another embodiment of the present invention.
Figure 18B:
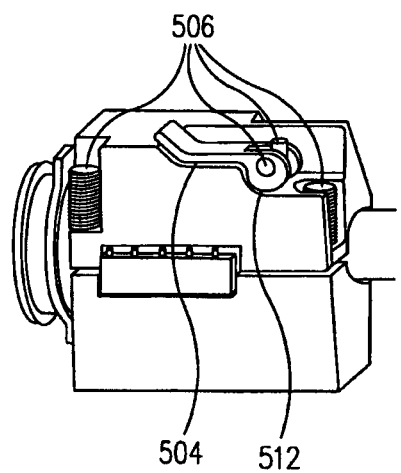
Figure 18C:
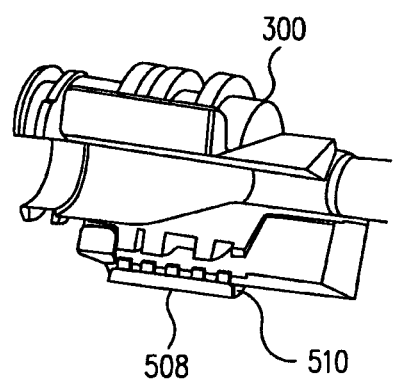

FIGS. 18A-18C illustrate views of a slide accessory clamp 500 holding cannula 300 in accordance with another embodiment of the present invention. A sterile drape portion between cannula 300 and clamp 500 effectively shielding clamp 500 from the sterile field is not shown. Clamp 500 includes two clamp jaws 502 and a lever portion 504 that actuates clamp jaws 502 from the open position to the closed position via a sliding movement. FIG. 18B shows nitronic pins 506 and lever handle 512 of lever portion 504 that is capable of moving over-center to lock-in the accessory between clamp jaws 502. FIG. 18C shows a magnet 508 and PCB with sensors 510 for sensing accessory identification information from identification rings of cannula 300.

Figure 19A:
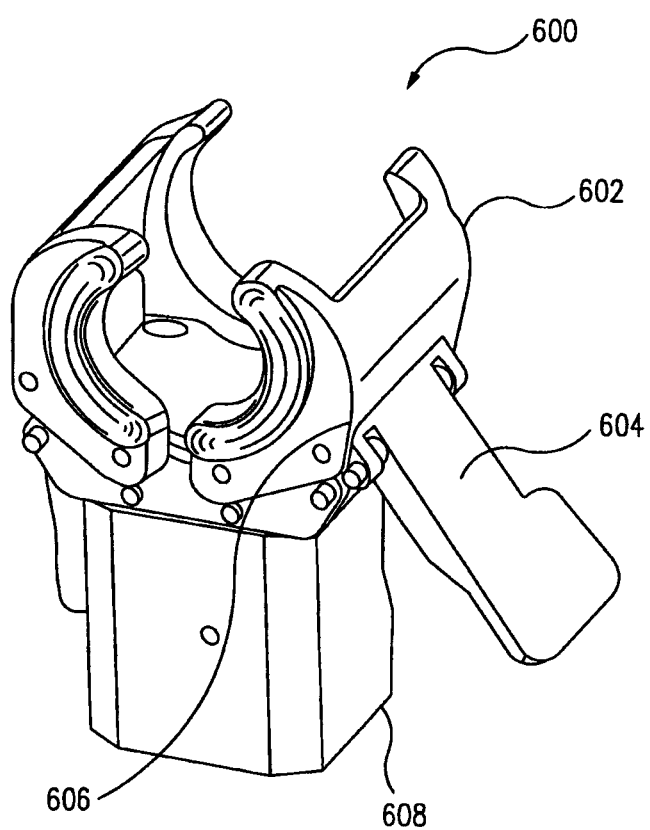
FIGS. 19A and 19B illustrate a pivot accessory clamp in accordance with another embodiment of the present invention.
Figure 19B:
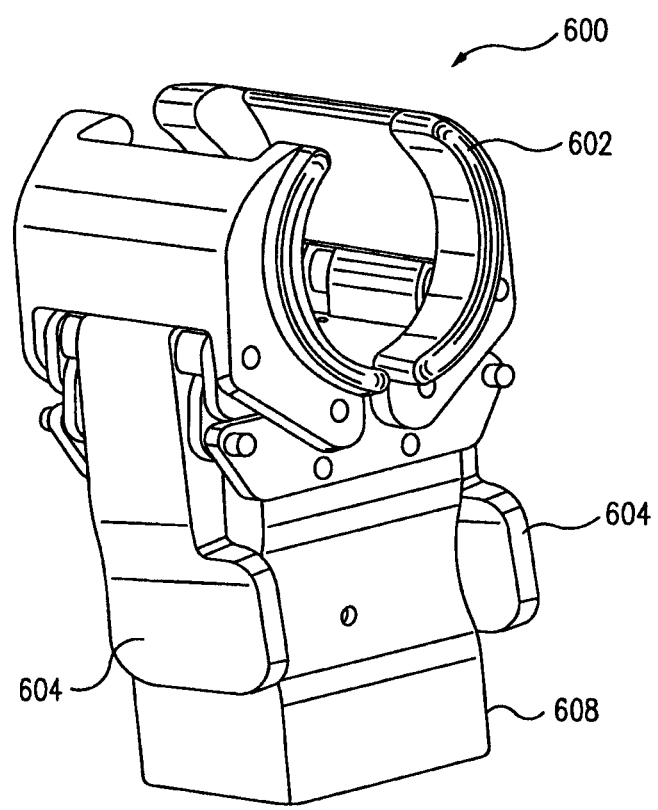

FIGS. 19A and 19B illustrate a pivot accessory clamp 600 in accordance with another embodiment of the present invention. A sterile drape portion between cannula 300 and clamp 600 effectively shielding clamp 600 from the sterile field is not shown. Clamp 600 includes two clamp jaws 602 and a lever handle 604 that is capable of moving over-center to lock-in the accessory between the clamp jaws. Clamp jaws 602 also include a detent 606 that is used to keep the lever open. Accessory clamp 600 further includes a base 608 in which sensors and attachment means may be included as described above with other embodiments.

Figure 20:
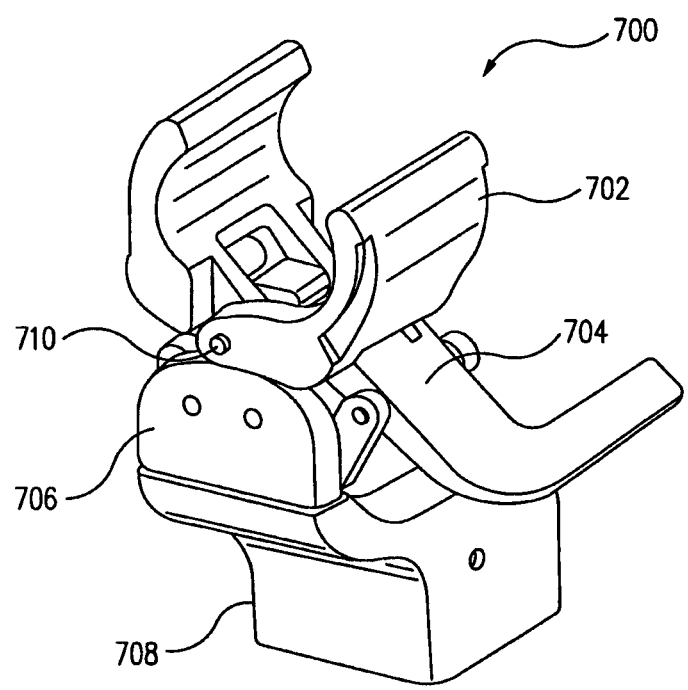
FIG. 20 illustrates another pivot accessory clamp in accordance with another embodiment of the present invention.

FIG. 20 illustrates another pivot accessory clamp 700 in accordance with another embodiment of the present invention. A sterile drape portion between cannula 300 and clamp 700 effectively shielding clamp 700 from the sterile field is not shown. Clamp 700 includes two clamp jaws 702 and a lever handle 704 that is also capable of moving over-center to lock-in the accessory between the clamp jaws. In this embodiment, base 708 includes a detent 706 that is used to keep the clamp jaws in the open position, and also may include sensors and attachment means as described above with other embodiments. Clamp 700 further includes a single pivot point 710 for both clamps to move between the open and closed positions, thereby allowing for a reduction in size of the clamp. Optionally, only one clamp needs to be opened to release the accessory.

Figure 21A:
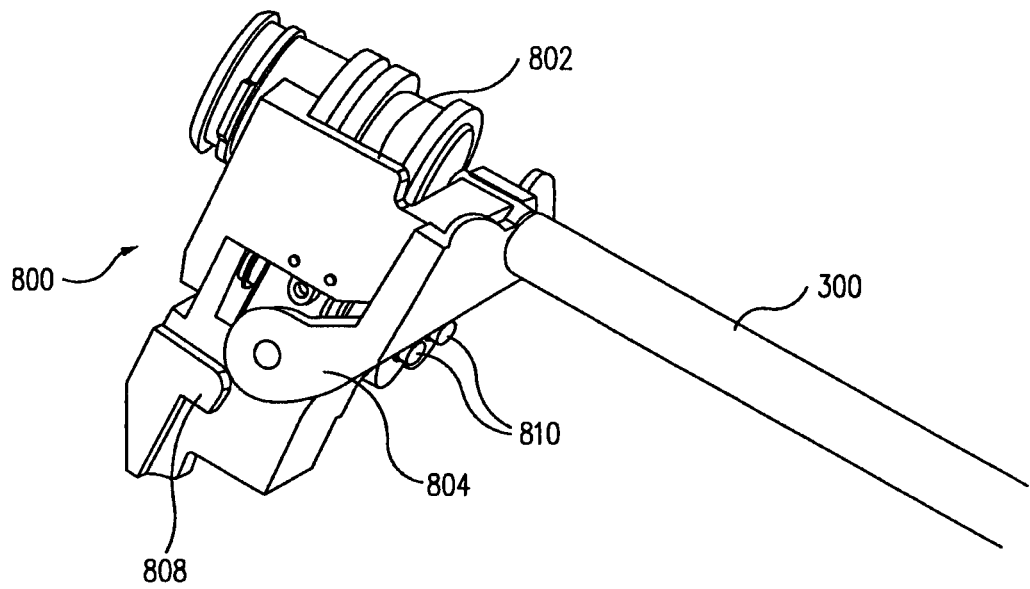
FIGS. 21A-21B illustrate another pivot accessory clamp in accordance with another embodiment of the present invention.
Figure 21B:
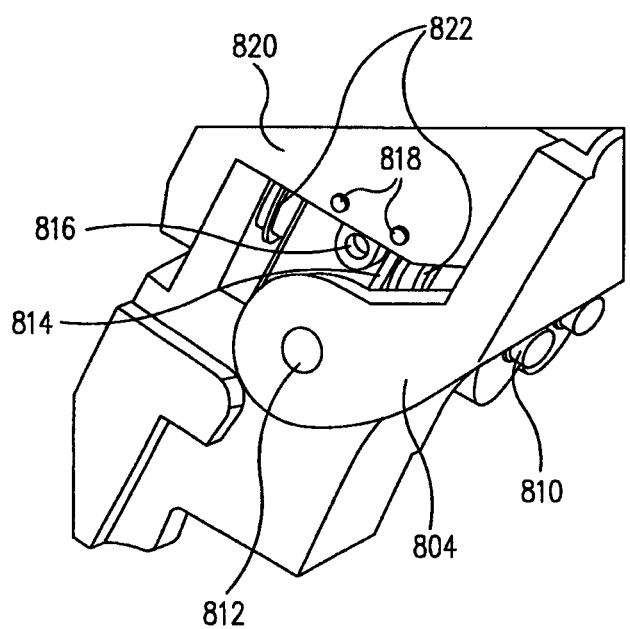

FIGS. 21A-21B illustrate a pivot accessory clamp 800 with captured cannula 300 in accordance with another embodiment of the present invention. A sterile drape portion between cannula 300 and clamp 800 effectively shielding clamp 800 from the sterile field is not shown. Clamp 800 includes two clamp jaws 802 and a lever handle 804 that moves from an open position to a closed position to lock-in the accessory between the clamp jaws. A lever portion further includes pivot pins 810 for pivoting the clamp jaws from an open position to a closed position. A base 808 may include attachment means for attaching clamp 800 to a robotic manipulator arm as described above with other embodiments. FIG. 21B illustrates a pivot pin 812 for the pivoting of lever handle 804, a cam follower 814 that rolls along the cam surface of the clamp 804, a spring plunger 816 that allows for some deflection of the cam follower while still transmitting force to the jaws, spring pins 818 to keep the spring plunger from coming out of the assembly, and torsion springs 822 that keep the pivoting clamp jaws 802 in the normally open position and allows the jaws to close when the lever handle 804 is moved. Clamp 800 further includes a sensor 820 for sensing accessory information from the accessory.

Figure 22A:
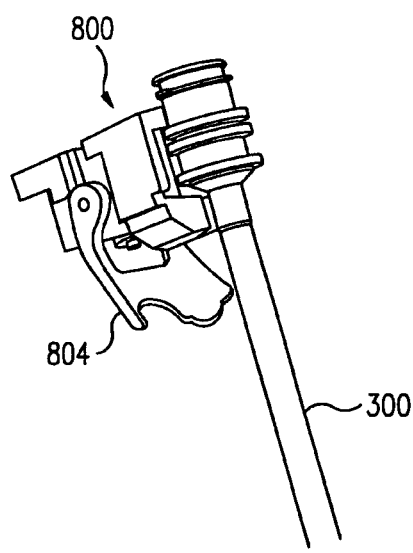
FIGS. 22A-22C illustrate perspective views for positioning and clamping a surgical accessory in the surgical accessory clamp of FIGS. 21A-21B in accordance with an embodiment of the present invention.
Figure 22B:
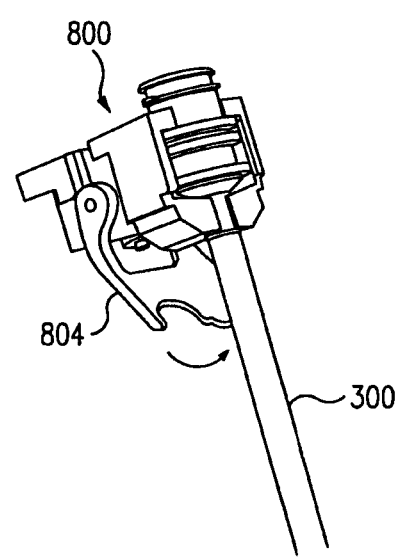
Figure 22C:
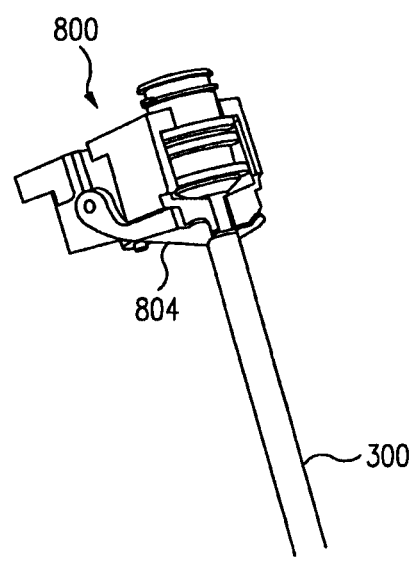

FIGS. 22A-22C illustrate perspective views for positioning and clamping surgical cannula 300 in surgical accessory clamp 800 of FIGS. 21A-21B in accordance with an embodiment of the present invention. Cannula 300 is positioned between clamps jaws in FIG. 22A. Lever handle 804 is pivoted until cam follower 814 clicks into a detent in FIG. 22B. Cannula 300 is then locked-in between the clamp jaws in FIG. 22C. Advantageously, the closed assembly may be manufactured to be no taller than the accessory such that the top surface of cannula 300 is flush with the top surface of accessory clamp 800 (i.e., a top surface of the clamp jaws).

Figure 23A:
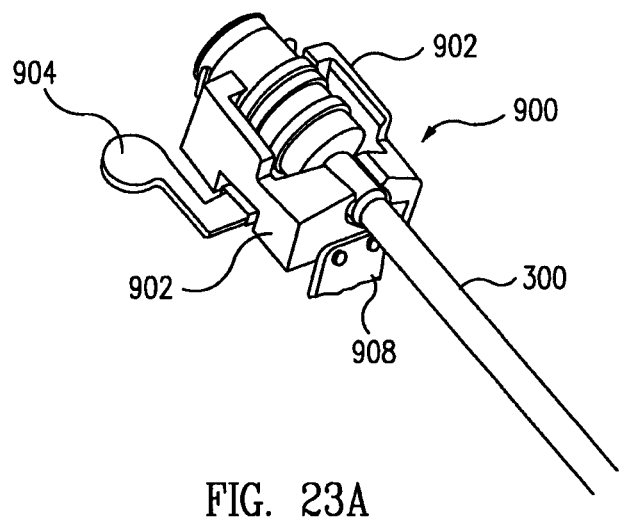
FIGS. 23A-23C illustrate another pivot accessory clamp in accordance with another embodiment of the present invention.
Figure 23B:
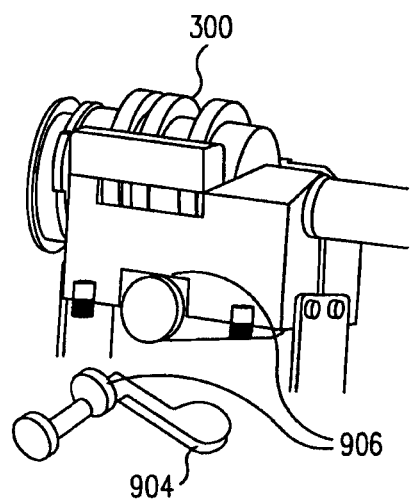
Figure 23C:
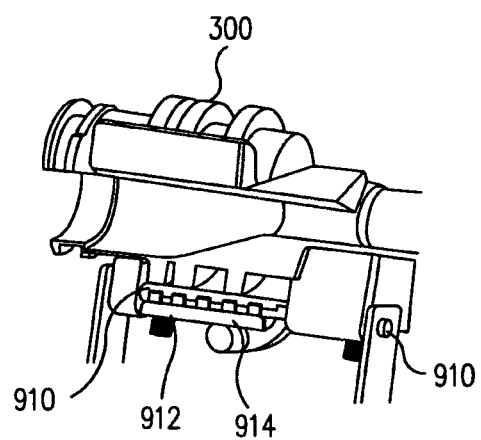

FIGS. 23A-23C illustrate a pivot accessory clamp 900 with captured cannula 300 in accordance with another embodiment of the present invention. A sterile drape portion between cannula 300 and clamp 900 effectively shielding clamp 900 from the sterile field is not shown. Clamp 900 includes two clamp jaws 902, a lever handle 904, and a base 908 for mounting clamp 900 to the distal end of a manipulator arm. FIGS. 23B and 23C show sections of clamp 900 including a detent 906 that is used to position lever handle 904 in place between open and closed positions. FIG. 23C shows pivot pin 910 for pivoting clamp jaws 902 between open and closed positions, and a magnet 912 and PCB with sensors 914 for sensing accessory information from the clamped accessory.

Figure 24A:
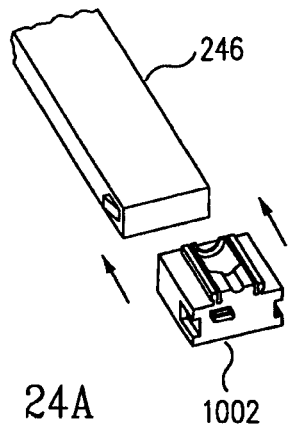
FIGS. 24A-24F illustrate perspective views for positioning and clamping a surgical accessory in a surgical accessory clamp in accordance with another embodiment of the present invention.
Figure 24B:
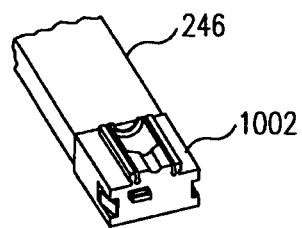
Figure 24C:
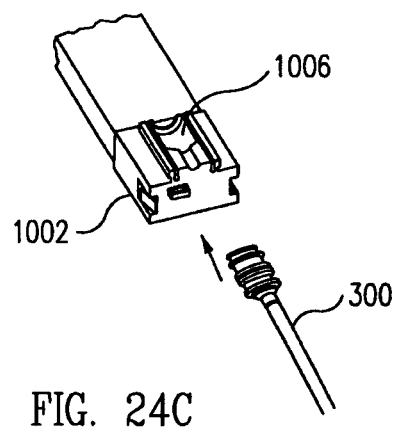
Figure 24D:
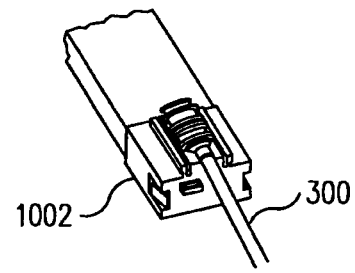
Figure 24E:
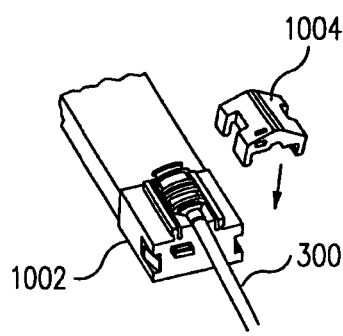
Figure 24F:
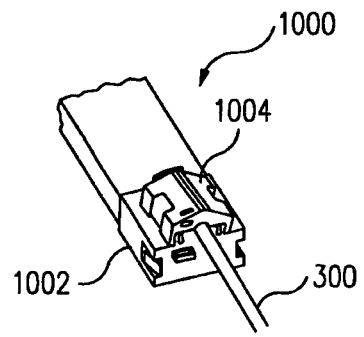

FIGS. 24A-24F illustrate perspective views for positioning and clamping cannula 300 in a surgical accessory clamp 1000 in accordance with another embodiment of the present invention. Accessory clamp 1000 includes a first mounting portion 1002 and a second mounting portion 1004 that capture or clamp cannula 300 therebetween. A sterile drape portion (not shown) may be positioned between first mounting portion 1002 and cannula 300. In another embodiment, the clamp components (e.g., the first mounting portion) may be part of the sterile drape and therefore be supplied sterile and then disposed of or re-sterilized for a later use. FIGS. 24A and 24B show first mounting portion 1002 is coupled to a distal end of a robot arm, such as forearm assembly 246, prior to or at the beginning of a surgical procedure. FIGS. 24C and 24D show cannula 300 being positioned over and onto first mounting portion 1002. First mounting portion 1002 includes a top surface 1006 that is shaped into a "pocket" to receive a portion of cannula 300. Although in this particular embodiment top surface 1006 is shaped into a portion of a cylinder to mate with the surface of the cylindrical accessory, other shapes and pockets are within the scope of the present invention. FIGS. 24E and 24F show second mounting portion 1004 placed over and coupled to first mounting portion 1002 with cannula 300 captured therebetween.

Figure 25A:
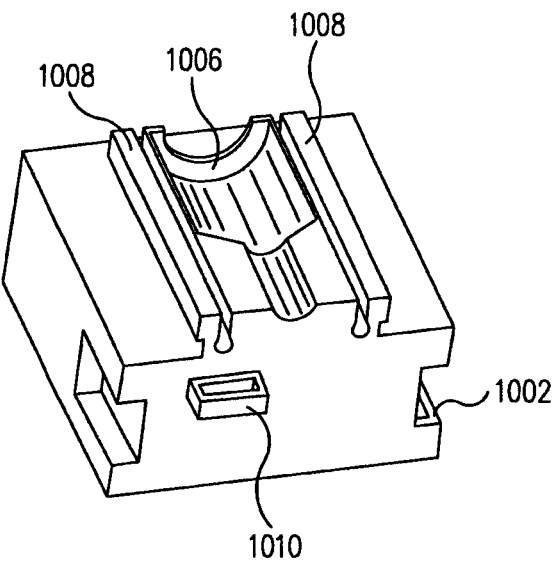
FIGS. 25A-25B illustrate perspective views of a first mounting portion in accordance with an embodiment of the present invention.
Figure 25B:
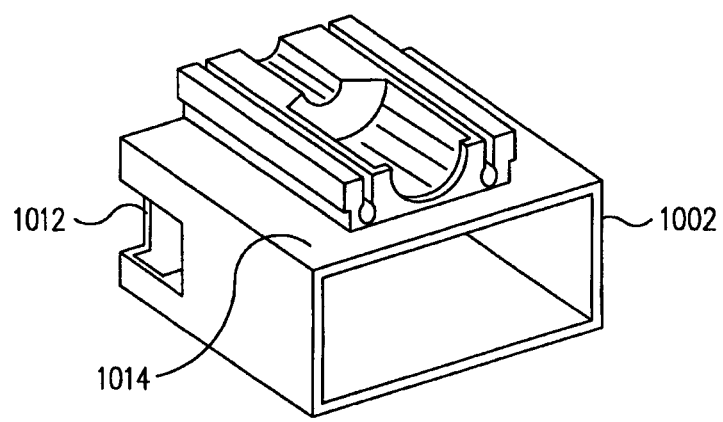

FIGS. 25A-25B illustrate perspective views of the first mounting portion 1002 in accordance with an embodiment of the present invention: FIG. 25A shows first mounting portion 1002 including retaining lips 1008 that mate with retaining lips on second mounting portion 1004. First mounting portion 1002 further includes a tether loop 1010 for connecting to second mounting portion 1004 via a cable (not shown) to keep the parts together for general ease of use. FIG. 25B shows first mounting portion 1002 including a slot 1012 for attaching the retaining clip and a lip 1014 for attaching the sterile drape.

Figure 26A:
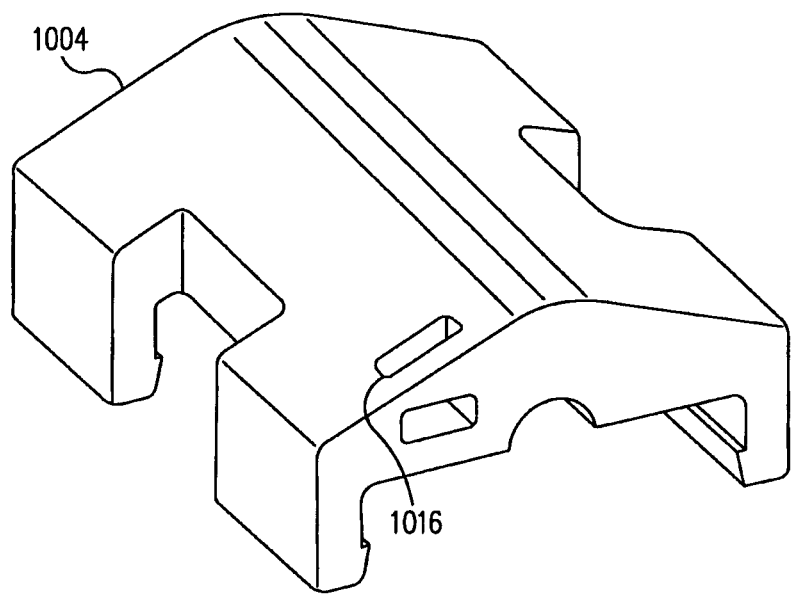
FIGS. 26A-26B illustrate perspective views of a second mounting portion in accordance with an embodiment of the present invention.
Figure 26B:
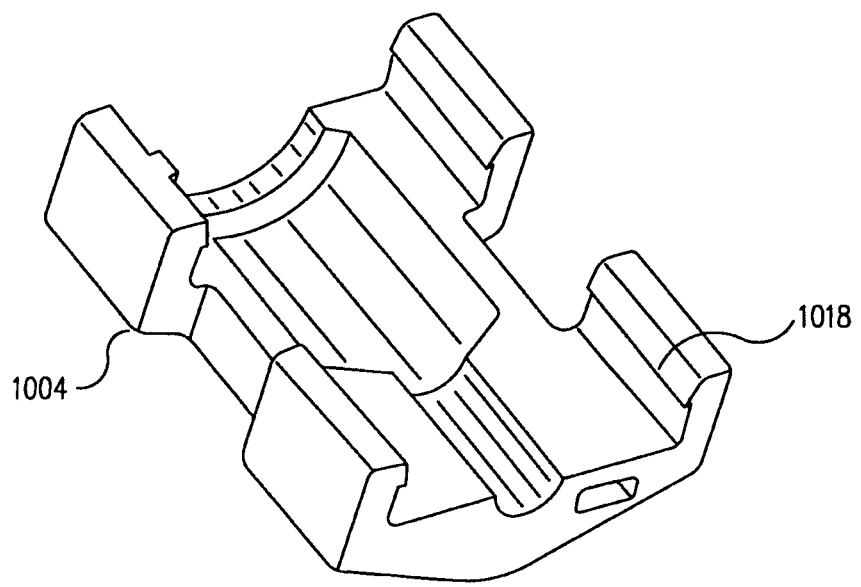

FIGS. 26A-26B illustrate perspective views of the second mounting portion 1004 in accordance with an embodiment of the present invention. FIG. 26A shows second mounting portion 1004 including a tether loop 1016 for connecting to tether loop 1010 of first mounting portion 1004 via a cable (not shown). Second mounting portion 1004 further includes retaining lips 1018 that mate with retaining lips 1008 on first mounting portion 1002.

Embodiments described above illustrate but do not limit the invention. It should also be understood that numerous modifications and variations are possible in accordance with the principles of the present invention. For example, although cylindrical shapes for the clamp jaws and drape portions are described in the embodiments above, other shapes and pockets for receiving non-cylindrical shaped accessories are within the scope of the present invention. Accordingly, the scope of the invention is defined only by the following claims.

We claim:

1. A robotic surgical system for performing a procedure within a sterile field, comprising:
    a manipulator arm; and
    a surgical accessory clamp for coupling a surgical accessory to a distal end portion of the manipulator arm, the accessory clamp including a base for coupling with the distal end portion of the manipulator arm, two clamp jaws with each of the clamp jaws directly and rotatably coupled to the base by a single pivot pin, and a rotatably coupled lever operable to move at least one of the clamp jaws, relative to the base, between an open position and a closed position, and
    a detent structure directly coupled to the base, the detent structure contacting a single clamp jaw to keep the surgical accessory clamp in the open position.

2. The robotic surgical system of claim 1, further comprising the surgical accessory, wherein the surgical accessory is a cannula defining an inner lumen for receiving a surgical tool and providing access through a percutaneous penetration.

3. The robotic surgical system of claim 1, further comprising the surgical accessory, wherein the surgical accessory is selected from the group consisting of a retractor, a stabilizer, and an endoscopic camera.

4. The robotic surgical system of claim 1, wherein a portion of a sterile drape covering the accessory clamp is a vacuum formed part of a larger drape or a separate molded portion of the larger drape and is formed to fit a shape of the two clamp jaws such that the portion of the sterile drape includes a surface shaped to receive the surgical accessory between the two clamp jaws.

5. The system of claim 1, further comprising a sterile drape covering the accessory clamp and the manipulator arm to shield the accessory clamp and the manipulator arm from the sterile field.

6. The robotic surgical system of claim 5, wherein the sterile drape over the accessory clamp includes a reinforcement portion.

7. The system of claim 1 wherein the two clamp jaws allow the surgical accessory to rotate along a length-wise axis in the open position.

8. The system of claim 1 wherein the two clamp jaws pivot about a single pivot axis provided by the single pivot pin.

9. The system of claim 1 further comprising a printed circuit board for processing information about the surgical accessory received between the two clamp jaws.

10. The system of claim 9 wherein the information includes identification of the surgical accessory.

11. A method of clamping a surgical accessory in a robotic surgical system, the method comprising:
    attaching a surgical accessory clamp to a distal end portion of a manipulator arm, the surgical accessory clamp including a base for attaching to the distal end portion of the manipulator arm, two clamp jaws with each of the clamp jaws directly and rotatably coupled to the base by a single pivot pin, and a rotatably coupled lever operable to move the two clamp jaws, relative to the base to which the lever is coupled by a lever pivot pin, between an open position and a closed position, wherein attaching the surgical accessory clamp comprises exerting a force to move at least one of the clamp jaws from an open position kept by a detent structure contacting a single clamp jaw to keep the surgical accessory clamp in the open position; and
    attaching an accessory within the clamp jaws.

12. The method of claim 11, further comprising introducing a surgical tool through the accessory.

13. The robotic surgical system of claim 5, wherein the sterile drape is comprised of material selected from the group consisting of HDPE, polyethylene, and polyurethane.

14. The method of claim 11 further comprising covering the manipulator arm and accessory clamp with a sterile drape to shield the manipulator arm and accessory clamp from a sterile field and attaching the accessory within the clamp jaws in the sterile field.

15. The method of claim 11, further comprising operating the lever to keep the surgical accessory clamp in the open position by changing a position or orientation of at least one of the clamp jaws with respect to a detent structure coupled to the base.

16. A robotic surgical system for performing a procedure within a sterile field, comprising:
    a manipulator arm;
    a surgical accessory clamp for coupling a surgical accessory to a distal end portion of the manipulator arm, the accessory clamp including a base for coupling with the distal end portion of the manipulator arm, two clamp jaws with each of the clamp jaws directly and rotatably coupled to the base by a single pivot pin, and a lever operable to move the two clamp jaws, relative to the base, between an open position and a closed position; and
    a detent structure directly coupled to the base, the detent structure contacting a single clamp jaw to keep the surgical accessory clamp in the open position.

17. The robotic surgical system of claim 16, wherein the lever is coupled to the base by a lever pivot pin that.

18. The robotic surgical system of claim 16, wherein the lever includes an over-center locking feature to hold the clamp jaws in the closed position.

19. The system of claim 16, further comprising a sterile drape covering the accessory clamp and the manipulator arm to shield the accessory clamp and the manipulator arm from the sterile field.

20. The robotic surgical system of claim 16, wherein a portion of a sterile drape covers the accessory clamp and is a part of a larger drape or a separate molded portion of the larger drape and is formed to fit a shape of the two clamp jaws such that the portion of the sterile drape includes a surface shaped to receive the surgical accessory between the two clamp jaws.

* * * * *